United States Patent [19]
Schulman et al.

[11] Patent Number: 6,067,474
[45] Date of Patent: May 23, 2000

[54] IMPLANTABLE DEVICE WITH IMPROVED BATTERY RECHARGING AND POWERING CONFIGURATION

[75] Inventors: Joseph H. Schulman, Santa Clarita; Robert Dan Dell, Canyon Country; Alfred E. Mann, Beverly Hills; Michael A. Faltys, Northridge, all of Calif.

[73] Assignees: Advanced Bionics Corporation; Alfred E. Mann Foundation for Scientific Research, both of Sylmar, Calif.

[21] Appl. No.: 09/126,615

[22] Filed: Jul. 31, 1998

Related U.S. Application Data
[60] Provisional application No. 60/054,480, Aug. 1, 1997.

[51] Int. Cl.[7] .................................................. A61N 1/34
[52] U.S. Cl. .................................................. 607/57; 607/33
[58] Field of Search .............................. 607/55, 56, 57, 607/33

[56] References Cited

U.S. PATENT DOCUMENTS

| | | |
|---|---|---|
| 3,942,535 | 3/1976 | Schulman . |
| 4,006,748 | 2/1977 | Schulman . |
| 4,041,955 | 8/1977 | Kelly et al. . |
| 4,134,408 | 1/1979 | Brownlee et al. . |
| 4,495,917 | 1/1985 | Byers . |
| 4,516,820 | 5/1985 | Kuzma ..................................... 339/48 |
| 4,991,582 | 2/1991 | Byers et al. . |
| 5,314,451 | 5/1994 | Mulier ....................................... 607/33 |
| 5,314,457 | 5/1994 | Jeutter et al. ........................... 607/116 |
| 5,411,537 | 5/1995 | Munshi et al. ............................ 607/33 |
| 5,411,538 | 5/1995 | Lin ............................................ 607/33 |
| 5,603,726 | 2/1997 | Schulman et al. ........................ 607/57 |
| 5,626,629 | 5/1997 | Faltys et al. .............................. 607/57 |
| 5,702,431 | 12/1997 | Wang et al. .............................. 607/33 |

FOREIGN PATENT DOCUMENTS

| | | |
|---|---|---|
| 0499939 | 8/1992 | European Pat. Off. . |
| 1197468 | 9/1968 | Germany . |
| 9837926 | 2/1998 | WIPO . |

Primary Examiner—Scott M. Getzow
Attorney, Agent, or Firm—Bryant R. Gold

[57] ABSTRACT

An implantable system, such as a neural stimulator or a cochlear implant system, includes a rechargeable battery configuration having improved recharging and lifetime characteristics. The battery is housed within the implant's case and has first and second electrode plates. Each electrode plate has a plurality of slits that extend across a substantial portion of the plate's surface area. The slits in the electrode plates reduce the magnitude of eddy currents induced in the plates by external ac magnetic fields allowing faster battery recharging times. Alternatively, the electrode plates are wrapped in a spiral configuration such that, in the plane of the spiral, the electrode plates have a small cross-sectional area and no closed current loops. Additionally, the implant device may be housed in a case formed of a high-resistivity material and a circuit included in the implant device is configured to avoid large current loops that would result in eddy current heating. As a backup option, the circuitry of the implant device may optionally be powered from an external battery that inductively couples energy to the same coil that is used to charge the internal battery. In one embodiment, the implantable system is partitioned into first and second implantable cases, each having electrical circuitry therein, and only one having a rechargeable power source therein, facilitating its subsequent replacement for repair or upgrading purposes. The two cases are coupled together when the system is in use. Coupling is achieved either magnetically and/or with a detachable electrical cable. In one embodiment, power is transferred from one implant case to the other using a 3-phase transmission scheme.

59 Claims, 9 Drawing Sheets

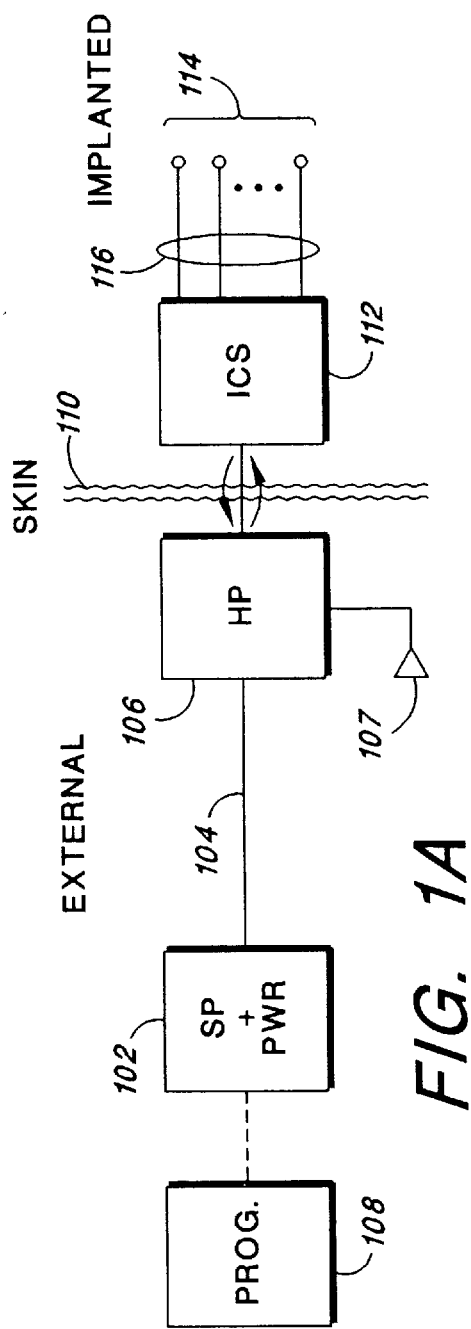
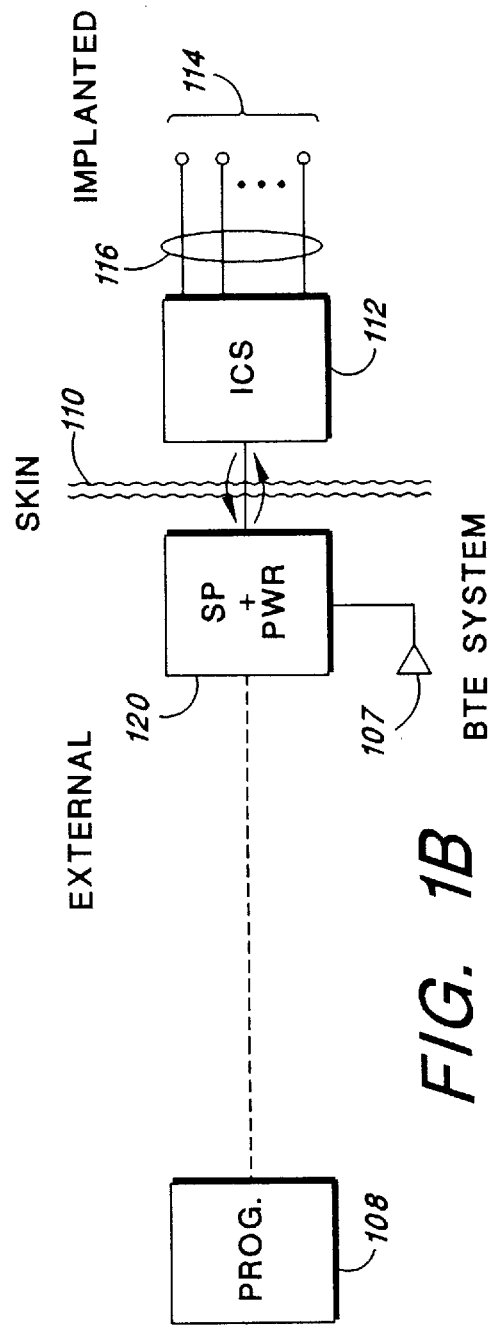
FIG. 1A
FIG. 1B

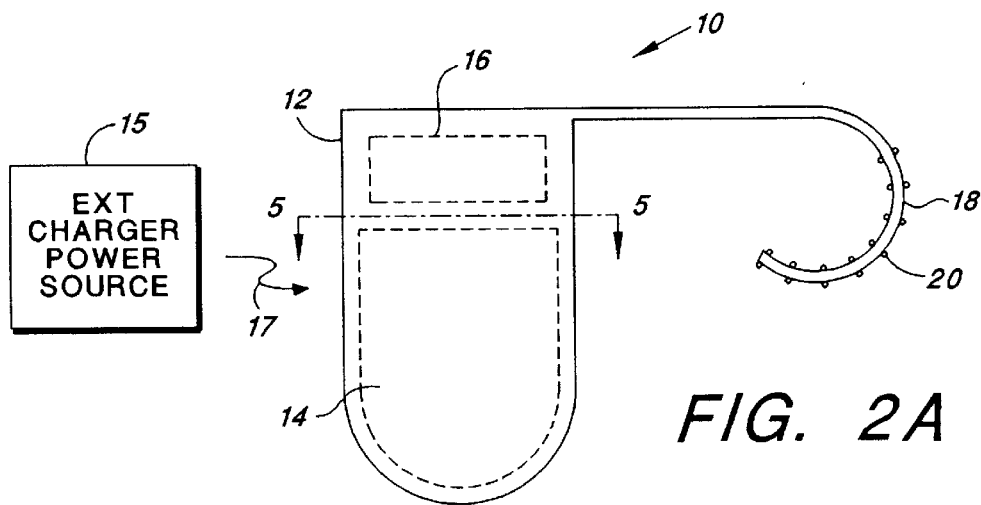
FIG. 2A
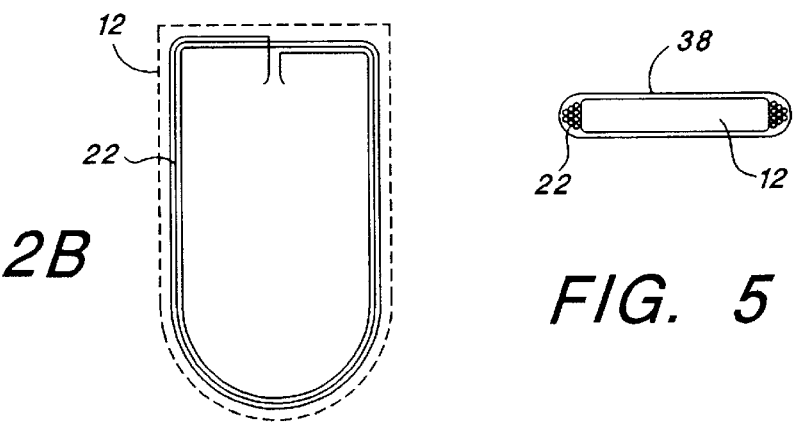
FIG. 2B
FIG. 5
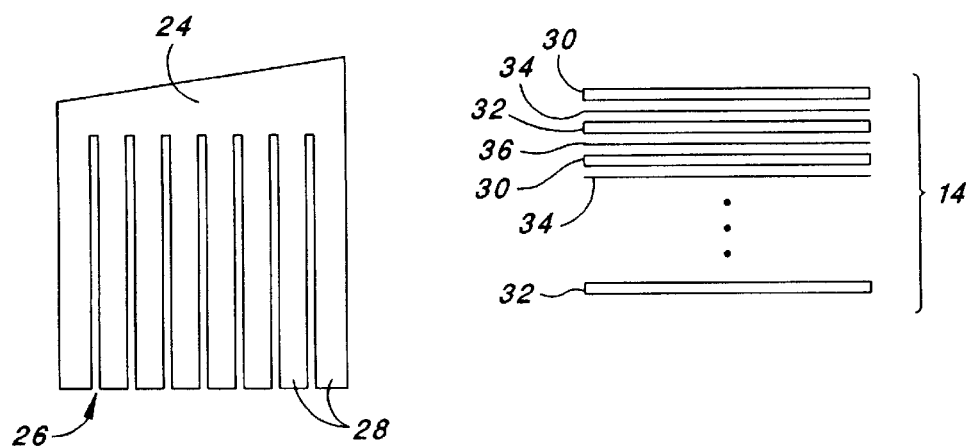
FIG. 3A
FIG. 4

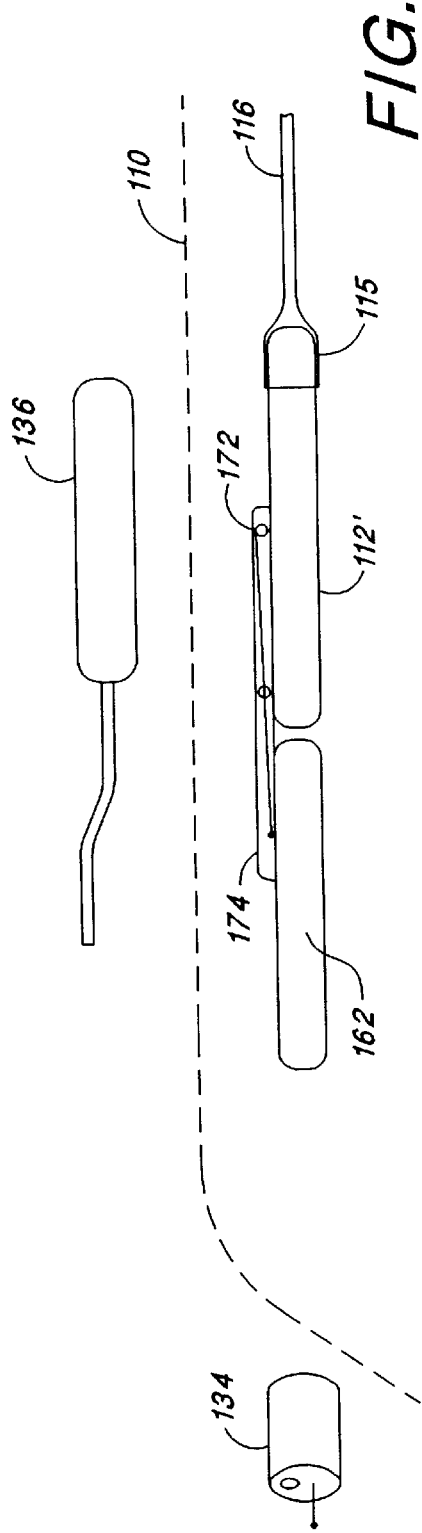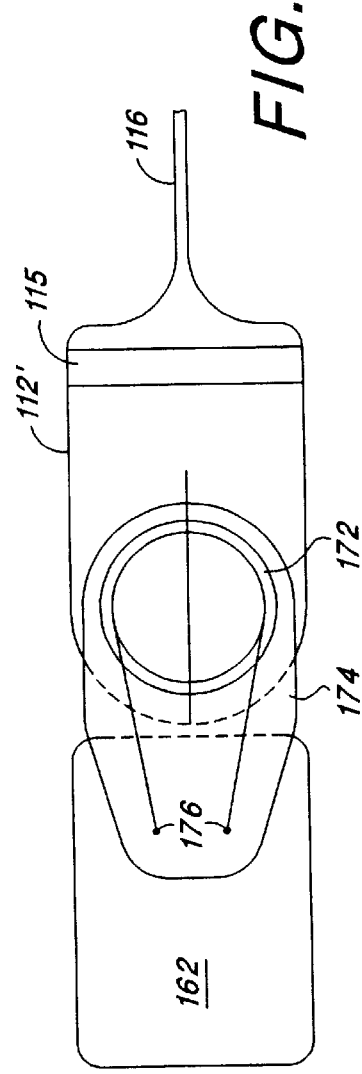
FIG. 14B
FIG. 14A

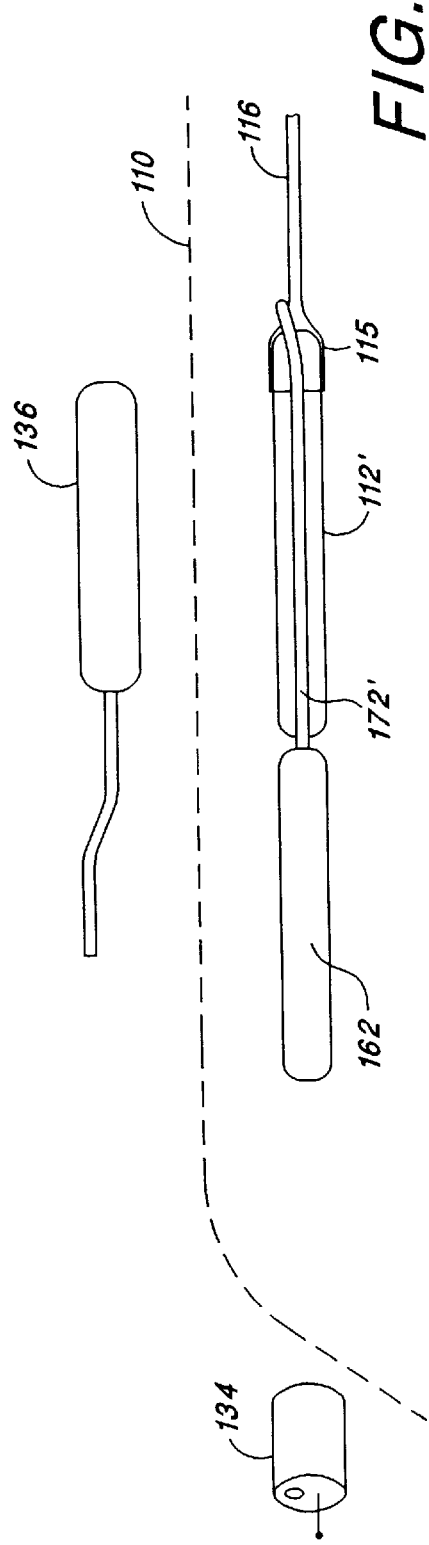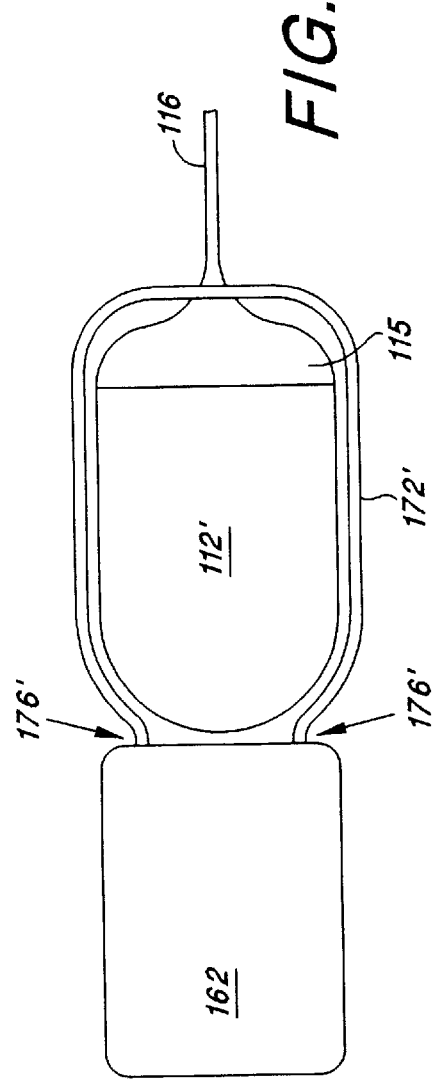

IMPLANTABLE DEVICE WITH IMPROVED BATTERY RECHARGING AND POWERING CONFIGURATION

The present application claims the benefit of U.S. Provisional Application Ser. No. 60/054,480, filed Aug. 1, 1997.

BACKGROUND OF THE INVENTION

The present invention relates to implantable devices, and more particularly, to a fully implantable device or system for stimulating or sensing living tissue wherein the implantable device has a rechargeable battery or other replenishable power source. One aspect of the invention relates to an implantable device configured to minimize heat generation due to eddy currents during battery charging and other magnetic powering. Another aspect of the invention relates to partitioning the circuit functions within the implantable system to allow upgrading the circuit functions and/or to permit existing partially implantable systems (having both implanted and external, or non-implanted, components) to be converted to fully implantable systems.

Presently available implantable stimulation devices, such as a cochlear implant device or a neural stimulator, typically have an implanted unit, an external ac coil, and an external belt-mounted control unit and power source. The external control unit and power source includes a suitable control processor and other circuitry that generates and sends the appropriate command and power signals to the implanted unit to enable it to carry out its intended function. The eternal control unit and power source is powered by a battery that supplies electrical power through the ac coil to the implanted unit via inductive coupling for providing power for any necessary signal processing and control circuitry and for electrically stimulating select nerves or muscles. Efficient power transmission through a patient's skin from the external unit to the implanted unit via inductive coupling requires constant close alignment between the two units.

Rechargeable implantable sensing and/or stimulation devices (e.g., heart pacemakers) are relatively bulky devices (e.g., 3 inches×2 inches×0.5 inches) and are quite heavy. Further, these rechargeable implantable devices require a substantial amount of charging time each week.

Accordingly, there exists a need for a small lightweight implantable device that does not require constant external power and that includes a long-lasting internal battery that may be recharged within a relatively short time period.

Further, there exists a need, should the battery within such a small, lightweight implantable device malfunction, or should the user desire to not use the internal battery for certain time periods, to still be able to provide power to the device, e.g., from an external power source, so that the device can continue to operate and provide its intended function, e.g., sensing and/or stimulating, to the patient, without having to implant a new device in the patient. Further, there exists a need for a fast, simple method for the battery module to be replaced during surgery, should replacement be necessary or desired.

Moreover, there are many patients who have received an implant system, e.g., a cochlear implant system of the type described in U.S. Pat. No. 5,603,726, incorporated herein by reference, which system includes both an implantable cochlear stimulator (ICS) attached to an electrode array that is inserted inside of the cochlea, and an external (non-implanted) battery, speech processor and headpiece. The speech processor (SP) and battery are housed within a wearable unit that is worn or carried by the patient, e.g., on a belt pack. The headpiece includes the external ac coil, a magnet, and a microphone. It is connected to the wearable unit via a cable. In use, the headpiece is positioned next to the external skin of the patient in close proximity to the ICS so as to provide efficient inductive coupling thereto. The magnet properly positions and holds the headpiece against the ICS implant location. Many of the patients who have and use the existing ICS system could greatly benefit from a fully implantable system, i.e., a system that eliminates the need for constantly wearing and/or carrying the external components of the system.

The present invention addresses the above and other needs.

SUMMARY OF THE INVENTION

The present invention is embodied in a rechargeable device, for implantation within living tissue, having improved battery recharging and lifetime characteristics. In some embodiments, the rechargeable device of the invention may be used to upgrade the ICS portion of existing implant systems to fully implantable systems. In other embodiments, the device is configured to minimize unwanted eddy currents that produce heat during battery recharging. Accordingly, the device may be recharged at a relatively fast rate thus minimizing disruptions to a patient's lifestyle. Once charged or recharged, the device may be used to power various implant configurations, including a fully implantable single unit, a wired system, or a proximity system.

Additionally, as a backup option or for diagnostic purposes, the rechargeable device may be continuously powered from a small, lightweight external unit, if necessary or desirable. Thus, in the event the internal (implanted) battery within the device malfunctions, or for whatever reason cannot be used, or the user or clinician (or other medical personnel) does not want to use it, it is still possible, through use of the lightweight external device, to provide operating power to the implantable device so that it may continue to provide its intended function (e.g., stimulating and/or sensing). Advantageously, by having such a backup option available, the patient may delay indefinitely battery-replacement and/or corrective surgery.

One embodiment of the invention, hereafter referred to as the "single unit" embodiment, resides in an implantable device having a case, a coil, electronic circuitry, and a rechargeable battery. The case forms a substantially hermetic housing and the coil surrounds the case to enclose a relatively large area and generates electrical power in the presence of externally induced ac magnetic fields passing through the coil's enclosed area. The rechargeable battery and electronic circuitry are housed within the case. The battery includes first and second electrodes for storing electrical power from the coil and for providing electrical power for the device. Each of the first and second electrodes has a relatively large surface area for electrical power storage that is configured to prevent current paths that are able to form relatively large current loops. Prevention of such current paths limits heat generating eddy currents in the electrode resulting from the magnetic fields passing through the coil's enclosed area that also pass through the battery.

Another embodiment of the invention, hereafter referred to as the "wired system" embodiment, resides in a fully implantable system that includes two implantable devices, each having its own case, jointed together by a detachable cable. A first of the implantable devices houses electronic circuitry for performing a desired function. A second of the implantable devices houses a rechargeable battery or other replenishable power source, and may also include additional circuitry. The second device provides operating power for the first implantable device. The detachable cable that connects the two devices may include transformer coupling on each end. Appropriate switching circuitry is included with the battery in the second device to convert the dc power of the battery to ac power for transmission to the first device. This ac power may be modulated, as desired, to also transmit information, e.g., control signals, from the second device to the first device. Thus, only ac power passes through the connecting cable.

Yet a further embodiment of the invention, hereafter referred to as the "proximity system" embodiment, resides in a fully implantable system that includes first and second implantable devices. The first device houses electronic circuitry for performing a desired function. The second device houses a rechargeable battery or other replenishable power source, and may also include additional circuitry. There is no direct electrical or physical connection between the first and second devices through which power and/or control signals are communicated from one device to the other. That is, there is no detachable cable that connects the two devices together as is the case with the "wired system" embodiment. Rather, power and control signals are inductively (magnetically) coupled from the second device to the first device in the same manner as is used to couple power and control signals between an external unit and an implanted unit in existing systems. Thus, one use of this proximity system embodiment allows a second device, housing a rechargeable battery and other circuitry that has heretofore been included in an external device, to be implanted proximate an implant device of an existing system, thereby effectively upgrading the existing system to a fully implantable system.

A variation of the invention that may be used with any of the above embodiments resides in an implantable device in which the case is formed of a relatively high resistivity material that similarly limits heat generating eddy currents in the case.

A further variation of the invention useable within any of the above embodiments includes a circuit, also housed within the case, that is laid out without forming relatively large current loops to limit heat generating eddy currents in the circuit.

The invention is also embodied in a rechargeable battery, subjected to externally induced ac magnetic fields, that includes a substantially hermetic housing and first and second electrodes, housed within the hermetic housing, for storing and providing electrical power. Each of the electrodes is configured to prevent forming relatively large current loops. More specifically, each electrode may be a relatively flat conductive plate lying substantially in a plane and having slits in the flat plate to reduce the area of closed loops in the plane of the plate. The first and second electrodes also may be conductive ribbons that are coiled into a spiral without forming a closed loop along the spiral. Alternatively, the first electrode may be formed of four ribbons connected in parallel and the second electrode may be formed of four ribbons connected in parallel. The four first electrode ribbons and the four second electrode ribbons are wrapped into a coiled spiral without forming a closed loop along the spiral. Also, the hermetic housing may be formed of a high-resistivity material to limit heat generating eddy currents in the housing.

Another embodiment of the invention resides in an implant device, e.g., a cochlear stimulation device or a neural stimulator device, having a relatively flat case, an electronic circuit housed within the case, a coil that surrounds the case, and a battery that is also housed in the case. The electronic circuit generates electrical pulses for stimulating, e.g., cochlear or other nerves, and the coil lies substantially in a plane parallel with case's flat portion and receives electrical power induced from external ac magnetic fields. The battery is coupled to the coil for battery recharging and has first and second electrode plates. Each electrode plate has a surface area that is relatively parallel to the plane of the flat case and that is configured to reduce the magnitude of eddy currents induced in the plate by the external ac magnetic fields during battery recharging.

In a specific embodiment of the invention, the surface areas of the first and second electrode plates are relatively flat and have a length of about 1 inch and a width of about 1 inch. Each electrode plate has a plurality of slits that extend across a substantial portion of the plate's surface area to produce regions of the surface area that each have a relatively long slender shape. All of the slits are substantially parallel and form a comb of conductive teeth. The conductive teeth have a width of about 0.040 inches and the slits have a width of about 0.001 inches and a length of about 0.900 inches. The slits form gaps, between the conductive teeth, that may be filled with an insulative material such as nylon, polypropylene, epoxy or other compatible insulating material.

In another embodiment of the invention, the case is formed of a metal material having a relatively high resistivity, such as the alloy Titanium$_{64}$ (6% aluminum, 4% vanadium), or Titanium$_{811}$ (8% aluminum, 1% molybdenum, 1% vanadium), and may be coated with an epoxy or plastic material. The cochlear implant device may further include a coil that encircles the case and that is embedded in the epoxy material, the coil for receiving externally induced ac power. The battery may be a rechargeable lithium ion battery and the device may further include a recharge control circuit that is connected between the coil and the battery for recharging the battery to specific voltage, such as 4.0 volts, or a specific amount of coulombs of electrical current using power induced or received through the coil. Alternatively, the device may further include a coulomb counter that measures the charge delivered to the battery during recharging and the charge delivered by the battery during discharge.

In yet another embodiment of the present invention, the device is an implant device that includes a case, a battery, and an implant lead that extends from the case. The lead has a plurality of electrodes for stimulating cochlear nerves within the cochlea, or stimulating other parts of the body. The battery is housed within the case and has first and second electrode plates. Each electrode plate has a surface area with a plurality of slits that extend across a substantial portion of the plate's surface area to produce areas having a relatively long slender shape. In comparison with a plate without slits of a similar surface area, the slitted electrode plates of the present invention reduce the magnitude of eddy currents induced in the plate by external ac magnetic fields. The reduced eddy currents allow greater magnetic fields with less heating to permit faster battery recharging times.

The present invention also resides in a method for recharging a battery within an implant device, e.g., within a cochlear implant device, that involves inducing an ac current in a coil that encircles the implant device, or that is contained within the implant device, or that is attached with two or more wires to the implant device, rectifying the induced ac current to produce dc current, and charging the battery using the dc current until the battery's voltage reaches a predetermined battery charge voltage or a predetermined coulomb value. For maximum battery lifetime for a lithium ion battery, the battery is charged to a voltage of no more than about 4.0 volts and is discharged to a voltage of no less than about 3.0 volts.

Such method for recharging may also be used, in accordance with another embodiment of the invention, to provide backup operating power to the implant circuitry in the event the internal rechargeable battery malfunctions, or is not to be used. Such backup powering may be accomplished, for example, using the same or a similar, small, lightweight external device, that is used for battery charging. Advantageously, having the option of providing backup power in this manner affords the patient the ability to defer indefinitely corrective- and/or battery-replacement surgery.

The backup powering option also allows greater flexibility in how the implant stimulation device is used. For example, in a cochlear implant device, it may be advantageous to change the speech processing strategy that is used to control the stimulation of the auditory nerves in the cochlea. Such speech processing strategy, in the first instance, is programmed inside of the implantable device. Should a new speech processing strategy be desired, and in the event reprogramming of the speech processing strategy within the implantable device is not feasible or possible, then a small, lightweight, behind the ear unit could be worn by the patient that incorporates the new speech processing strategy, and powers and controls the implanted stimulation circuitry within the implantable device to apply the new stimulation strategy.

The invention further includes an implant system consisting of two packages. In one specific embodiment, the first package includes the coil, battery, battery charging and power regulation circuitry and some of the electronics circuitry (signal handing and processing circuitry) that may potentially need to be updated or upgraded in the future as new signal processing and data handling technologies evolve. The second package includes the wires going to the stimulation and sensing electrodes and devices, and the interface circuitry for stimulating and sensing, as well as other signal processing and conditioning circuits which are intimately associated with the stimulation and sensing functions performed within the second package, and which are not likely to change or need to be updated or upgraded as new technologies evolve. Thus, the first package is a package that can, if needed, be replaced or upgraded at a future time through minor replacement surgery. The second package is a package that, once implanted, should not ever need replacing or upgrading.

Also, in both the first and second packages, circuitry is included to permit capacitive coupled data transmission and reception circuits that are used to transfer data and power between the two packages. The packages can be connected with a detachable cable ("wired system") or can be coupled together through induction coupling ("proximity system"). In the wired system, by way of example, data may be transferred between the two packages on two or three wires, while power may be transferred on three wires via a capacitor-coupled 3-phase square wave signal that does not allow dc current to flow outside of the hermetic seal of the packages. The 3-phase signal, when received at the other package, can simply be recombined to create a DC signal using synchronized switching without the need for filtering capacitors and with negligible ripple. In the proximity system, power is transferred via an ac carrier signal, and data is transferred by modulating the carrier signal.

BRIEF DESCRIPTION OF THE DRAWINGS

The above and other aspects, features and advantages of the present invention will be more apparent from the following more particular description thereof, presented in conjunction with the following drawings wherein:

FIG. 1A illustrates a typical cochlear stimulation system as currently used by many patients, including an implantable cochlear stimulator (ICS) that is inductively coupled with an external headpiece (HP) connected with an external speech processor (SP) and power source.

FIG. 1B illustrates a behind-the-ear (BTE) cochlear stimulation system that includes an implanted cochlear stimulator (ICS) and an external BTE unit that includes a power source, a speech processor and a microphone.

FIG. 2A is a plan view of a representative single unit, fully implantable, cochlear implant device in accordance with the present invention.

FIG. 2B is a plan view of an AC power pickup coil for use in recharging a battery of the cochlear implant device of FIG. 2A.

FIGS. 3A, 3B and 3C are plan views of exemplary battery electrode plates for reducing induced eddy currents on the plates, in accordance with the present invention.

FIG. 4 is an elevation view of a battery electrode plate and separator stack.

FIG. 5 is a cross-sectional view, taken along line 5—5 of FIG. 1, showing an epoxy coating covering the cochlear implant device.

FIGS. 14A and 14B are a plan and profile (side) view, respectively, of one embodiment of a fully implantable, partitioned, proximity system made in accordance with the invention.

FIGS. 15A and 15B are similarly a plan and profile view, respectively, of another embodiment of a fully implantable, partitioned, proximity system.

Corresponding reference characters indicate corresponding components throughout the several views of the drawings.

DESCRIPTION OF THE PREFERRED EMBODIMENTS

Figure 1C:
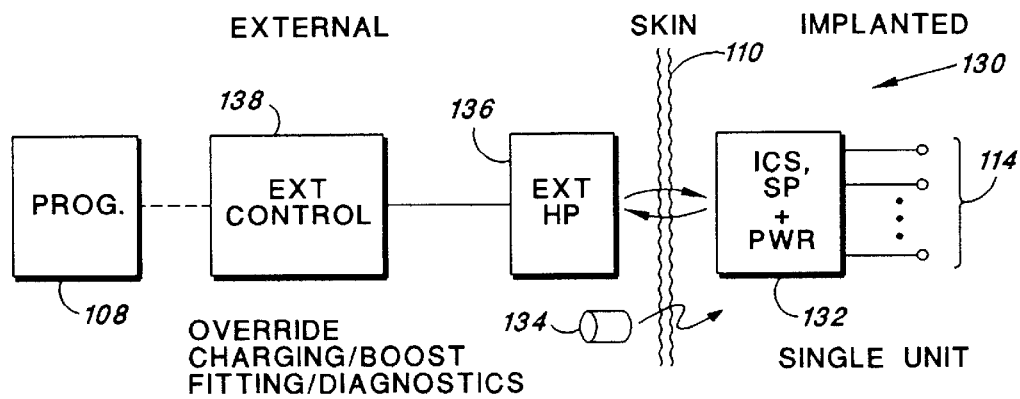
FIG. 1C shows one type of a single unit, fully implantable system made in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

Overview

The present invention relates to a fully implantable device having a rechargeable battery (or other power source). In a preferred embodiment, the implantable device comprises a fully implantable cochlear stimulation system, and thus such a cochlear stimulation system is described herein. It is to be understood, however, that the present invention may also be used with other types of implantable systems, and is not intended to be limited to just a cochlear stimulation system. Any medical or other device or system which must be implanted in living tissue, or a similar environment, and which requires operating power from a replenishable power source, such as a rechargeable battery, and wherein the operating power must be inductively or magnetically or otherwise coupled into the implantable device without a direct electrical connection, may benefit from the application and teachings of the present invention.

To better understand and appreciate the present invention, it will be helpful to briefly review current or existing cochlear stimulation systems, which are representative of all tissue-stimulating systems. A representative cochlear stimulation system of the type currently used by many patients is fully described, e.g., in U.S. Pat. No. 5,603,726, previously referenced and incorporated herein by reference. As described in the '726 patent, and as illustrated in FIG. 1A, such existing system includes implanted and external components. The external components include a speech processor (SP), a power source (e.g., a replaceable battery), and a headpiece (HP) 106. The SP and power source are typically housed within a wearable unit 102 that is worn or carried by the patient. The wearable unit is electrically connected to the HP 106 via a cable 104. A microphone 107 is also included as part of the headpiece 106.

The implanted components include an implantable cochlear stimulator (ICS) 112 and an array of electrodes 114. The electrode array 114 is intended for implantation within the cochlea of the patient. The ICS 112 is implanted behind the ear, so as to reside near the scalp. The electrode array 114 is permanently connected to the ICS by way of a multi-conductor implantable cable 116.

Inside of the headpiece 106 is a coil that is used to inductively or magnetically couple a modulated ac carrier signal to a similar coil that is included within the ICS 112. In order to achieve efficient coupling, without suffering significant losses in the signal energy, it is important that the external coil within the headpiece be properly aligned with the internal coil inside the ICS. To achieve proper alignment, a magnet is typically included within both the headpiece 106 and the ICS 112, and the resulting magnetic attraction between the two magnets not only aligns the coils, as desired, but also provides a holding force that maintains the headpiece 106 securely against the scalp or skin 110 of the patient.

In use, a carrier signal is generated by circuitry within the wearable unit 102 using energy derived from the power source within the speech processor unit 102. Such carrier signal, which is an ac signal, is conveyed over the cable to the headpiece 106 where it is inductively coupled to the coil within the ICS 112. There it is rectified and filtered and provides a dc power source for operation of the circuitry within the ICS 112. Sounds are sensed through the external microphone 107, amplified and processed by circuitry included within the speech processor unit 102, and converted to appropriate stimulation signals in accordance with a selected speech processing strategy by circuitry within the speech processor unit 102. These stimulation signals modulate the carrier signal that transfers power to the ICS 112. The ICS includes an appropriate demodulation circuit that recovers the stimulation signals from the modulated carrier and applies them to the electrodes within the electrode array 114. The stimulation signals identify which electrodes, or electrode pairs, are to be stimulated, and the intensity of the stimulation.

Some embodiments of the ICS 112, as indicated in the '726 patent, include a backtelemetry feature that allows data signals to be transmitted from the ICS 112 to the headpiece 106, and hence to the Speech Processor 102. Such backtelemetry data provides important feedback information to the speech processor regarding the operation of the ICS.

When adjustment or fitting or other diagnostic routines need to be carried out, an external programming unit 108 is detachably connected to the SP unit 102. Through use of the external programmer 108, a clinician, or other medical personnel, is able to select the best speech processing strategy for the patient, as well as set other variables associated with the stimulation process. See, e.g., U.S. Pat. No. 5,626,629, incorporated herein by reference, for a more detailed description of a representative fitting/diagnostic process.

Although the system shown in FIG. 1A has been of great value and benefit to many patients who could not otherwise experience the sensation of hearing, there are several drawbacks associated with use of the system. For example, the wearable unit 102 must be worn or carried by the patient, and the cable 104, which may be up to one meter long, must be routed from the unit 102 to the headpiece 106. Some patients find wearing the unit 102 to be inconvenient, and find the use of the headpiece 106, with its cable 104, to be unsightly and uncomfortable.

In order to eliminate the need for the cable 104, a behind-the-ear (BTE) unit 120 may be used, as illustrated in FIG. 1B. The BTE unit 120 includes everything that was previously included within the wearable unit 102, only in a much smaller volume. The BTE unit 120 thus includes a suitable power source, as well as circuitry for performing a desired speech processing function. With the BTE unit 120, there is thus no need for the cable 104, and the patient simply wears the BTE unit behind his or her ear, where it is hardly noticed, especially if the patient has hair to cover the BTE unit.

Advantageously, the batteries employed within the wearable unit 102 (FIG. 1A) or the BTE unit 120 (FIG. 1B) may be readily replaced when needed. Still, the BTE unit 120 may become uncomfortable to wear when worn for long periods of time, and must be removed at certain times, such as when swimming or bathing. Some patients would thus like the convenience of being able to hear at all times, including when swimming or bathing, and thus a fully implantable stimulation system is desired.

The present invention is directed to fully implantable devices and systems that employ a rechargeable battery or other replenishable power source. While it is known in the art to use an implantable stimulating device with a rechargeable battery, see, e.g, applicant Schulman's earlier U.S. Pat. No. 3,942,535, such recharging systems require a bulky external recharging system, and are time consuming to use. In contrast, the present invention provides a rechargeable battery, and method of recharging the battery, that allows the recharge operation to occur quickly and conveniently, without significant impact on the patient's lifestyle.

The present invention also allows different implant configurations to be used as part of the fully implantable system, including the ability to use the ICS 112 of the prior systems in a fully implantable system.

A fully implantable single unit system 130 made in accordance with the invention is shown in FIG. 1C. As illustrated in FIG. 1C, such system 130 includes the ICS circuitry, the speech processor circuitry, and a power source within a single unit 132. An electrode array 114 is connected to the single unit 132 in conventional manner. For the embodiment shown in FIG. 1C, a microphone 134 is coupled via a telecoil link to the single unit 132. Such telecoil link powers the microphone circuits through magnetic coupling from the unit 132. Sounds sensed by the microphone 134 are transmitted to the unit 132 via an rf transmitter built-in to the microphone 134. (The transmission distance for such signal is very short, only a centimeter or two, so not much power is needed for such transmission.) Advantageously, such microphone 134 is inserted inside the ear canal so it is not visible externally.

Other types of microphones may also be used with the implant unit 132. For example, externally-generated sound waves may be sensed through the patient's skin and case of the single unit 132 at locations where the case shell is properly supported and of the proper thickness.

When the battery included within the single unit 132 needs to be recharged, which may only be a few minutes a day, or a few times during the week, an external headpiece 136 is placed adjacent the unit 132, and inductive coupling is used to transfer charging power to the unit's battery. The external headpiece, in turn, connects to an external control unit 138, which may, in turn, derive its power from replaceable batteries or from an ac power plug. When programming and/or diagnostic tests are needed, an external programmer 108 may be detachably connected to the external control unit 138.

The external control unit 138 is thus used to charge/ recharge the battery within the implanted unit 132, as well as for other purposes. For example, the external control unit 138 may be used to override the internal speech processor with an external speech processor, e.g., a speech processor included within the external programmer 108. Further, the external control unit 138 may be used to boost the power provided by the internal battery. The external control unit 138 may also be used for programming the implant device 132, e.g., fitting the ICS after implant or adjusting the stimulation parameters of the fully implantable unit 132, as well as for diagnostic purposes.

For the embodiment 130 shown in FIG. 1C, as well as for the other embodiments shown in FIGS. 1D and 1E, discussed below, it is to be understood that backtelemetry may be employed to allow data signals to be sent from the implanted unit to the external headpiece 136, and hence to the external control unit 138.

Figure 1D:
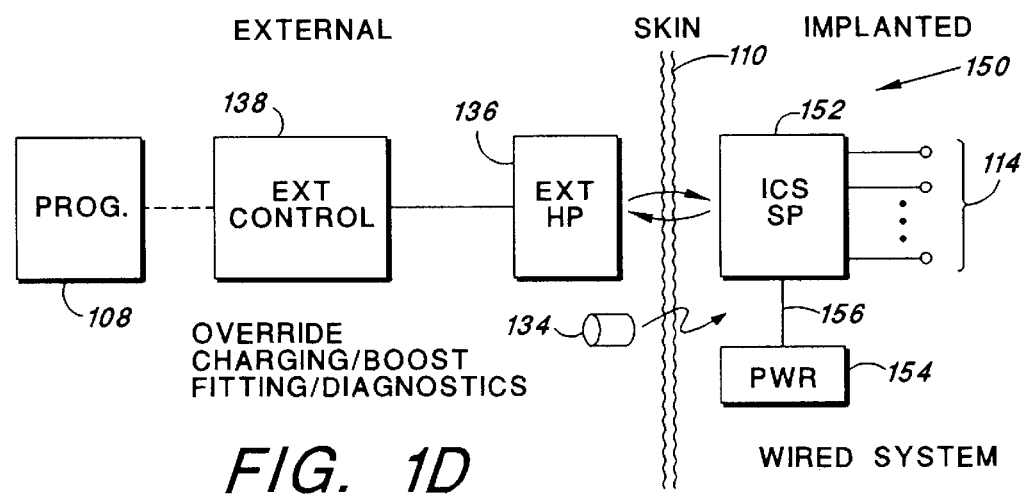
FIG. 1D shows one type of a fully implantable, partitioned, wired system in accordance with the invention.

Turning next to FIG. 1D, a "wired system" embodiment 150 of the invention is depicted. In such wired system 150, at least two separate implantable units 152 and 154 are employed and the circuits of the system are partitioned between the two units. In a first unit 152, for example, speech processor (SP) and ICS circuitry are housed, and such unit is permanently connected to an electrode array 114. In a second unit 154, a battery, or other suitable power source, is housed. The second unit 154 is electrically connected to the first unit 152 via a detachable cable 156. In a preferred embodiment, only ac power is coupled from the power unit 154 to the SP/ICS unit 152, thereby preventing any possibility that a dc current might flow through the tissue through which the cable is routed. This is important because a dc current could cause damage to the tissue, whereas an ac current will not. Also, because the cable is not hermetically insulated from the surrounding tissue, it is very possible that minor leakage current could flow through the tissue if it carried dc currents.

The second unit 154 includes appropriate switching circuitry that converts the dc power associated with the battery (or other power storage element) therein to an ac signal for coupling to the first unit 152. Also, appropriate circuitry is employed to allow ac power induced into the unit 152 from the external headpiece 136 to be directed to the battery in the unit 154 in order to charge the battery.

Although the preferred power source for use within the fully implantable systems described herein is a rechargeable battery, it is to be understood that other power sources may also be employed. For example, an ultracapacitor (also known as a supercapacitor) may be used. An ultracapacitor, like a conventional capacitor, allows an electric charge (voltage potential) to be stored therein. Unlike a regular capacitor, the energy density of the ultracapacitor is orders of magnitude greater than the energy density of a normal capacitor, thereby allowing a great amount of energy to be stored in the ultracapacitor. This stored energy may then be withdrawn from the ultracapacitor for subsequent use. Thus, for this type of application, where recharging must occur on a regular basis, and when appropriate discharge circuits are employed to control the rate of discharge or energy withdrawal, the ultracapacitor provides a viable alternative to a rechargeable battery for use within the implantable system.

A suitable microphone, e.g., a complete-in-cannel (CIC) microphone 134 of the type described previously, is used to sense sounds and couple signals representative of such sounds to the speech processor (SP) circuits within its respective implantable portion.

It should be noted that the partitioning illustrated in FIG. 1D, which shows that the ICS and SP circuitry are included within the first implantable unit 152, and which shows that the power source, e.g., rechargeable battery, is included within the second implantable unit 154, such partitioning is only exemplary. For some embodiments, for example, the SP circuitry may be included within the second implantable unit 154, leaving only the ICS circuitry within the first implantable unit 152.

The advantage of the wired system 150 shown in FIG. 1D is that a fully implantable system is provided wherein one of the two implantable units, e.g., the power unit 154, may be replaced, if necessary, through only minor surgery. As indicated, the cable 156 that connects the second unit 154 to the first unit 152 is detachable. The implantable connector that connects the cable 156 to the unit 154, may be of any suitable type, e.g., of the type commonly used with implantable pacemakers, or of the pressure type shown in U.S. Pat. No. 4,516,820 (Kuzma), incorporated herein by reference, or of the type shown in U.S. Pat. No. 4,495,917 (Byers), also incorporated herein by reference.

The external headpiece 136 and external control unit 138, and programmer 108, may be used with the wired system embodiment 150 shown in FIG. 1D in the same manner as these components are used with the single unit embodiment 130 shown in FIG. 1C.

Figure 1E:
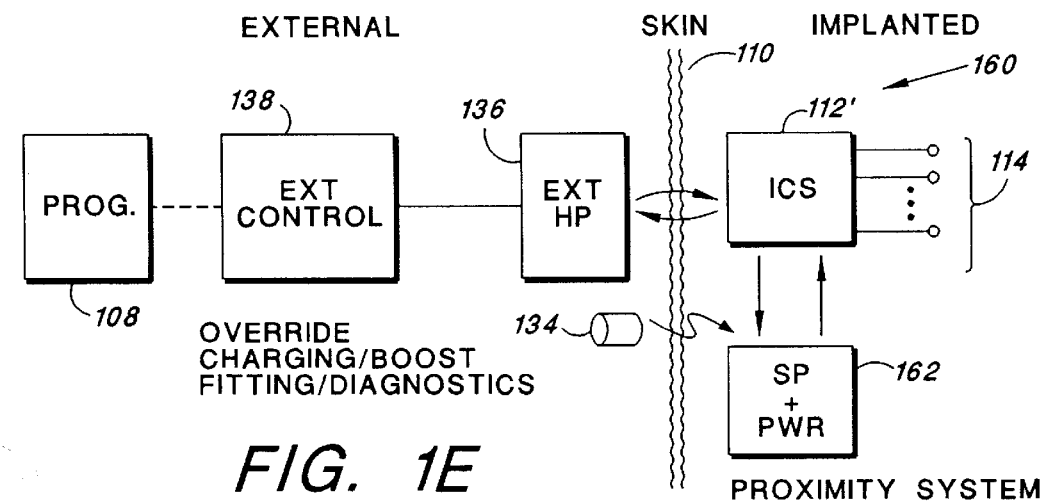
FIG. 1E shows one type of a fully implantable, partitioned, proximity system in accordance with the invention.

Turning next to FIG. 1E, a partitioned proximity system 160 is shown that is similar to the wired system 150 shown in FIG. 1D, but without the use of a connecting cable 156 between the two units. As seen in FIG. 1E, a first implantable unit 112' comprises an ICS with an electrode array 114 connected thereto. An advantage of the proximity system 160 is that the first implantable unit 112' may be substantially the same as, or identical to, that of the ICS 112 used in existing cochlear stimulation systems (see FIG. 1A or FIG. 1B). This allows existing stimulation systems having an ICS 112 to be upgraded to a fully implantable system as shown in FIG. 1E. A second implantable unit 162 includes speech processor (SP) circuits and a power source, e.g., a rechargeable battery. The second unit 162 is implanted so as to be in close proximity to the first unit 112'. A coil associated with the second unit 162 is aligned with the coil included within the ICS 112', e.g., as shown below in connection with the description of FIGS. 14A–16. This allows inductive coupling to occur between the implantable units 112' and 162 in the same manner as occurs between the BTE unit 120 and the ICS 112 shown in FIG. 1B, or between the headpiece 106 and the ICS 112 shown in FIG. 1A.

A suitable microphone, e.g., an complete-in-cannel (CIC) microphone 134 of the type described previously, is used to sense sounds (pressure waves) and couple electrical signals representative of such sounds to the speech processor (SP) circuits within the implantable portion 162.

The external headpiece 136 and external control unit 138, and programmer 108, may be used with the partitioned proximity system embodiment 160 shown in FIG. 1E in the same manner as used with the single unit embodiment 130 shown in FIG. 1C and the partitioned wired system embodiment 150 shown in FIG. 1D.

By using the system shown in FIG. 1E, it is seen that the following advantages are achieved: (1) older implants, i.e., existing ICS units 112, may be upgraded to fully implantable systems without replacing the implant unit 112 and electrode 114; (2) implantable systems may be upgraded with improved battery (or other power source) technology and lower-power more-sophisticated SP circuits, as such become available, with only minor surgery for the patient; (3) batteries can be replaced with only minor surgery, as required; and (4) charging, override, power boost, fitting and diagnostics may be performed by simply overriding the implanted SP circuits with an external speech processor.

Improved Battery Charging

Next, the techniques employed by the invention to make the charging of the battery more efficient will be described. Such description, in general, is presented in connection with a single unit system 130 of the type shown in FIG. 1C, adapted for use as a cochlear stimulator. It is to be understood, however, that such techniques are equally applicable to any of the other embodiments of the invention described herein.

With reference to FIG. 2A, it is seen that the invention is embodied in an implant device 10 having a case 12, an internal battery 14, and an internal circuit 16 that are configured for improved battery charging time and lifetime characteristics. The battery's charging time is largely limited by the amount of heat generated during battery charging. During charging, a significant amount of heat may be generated by eddy currents induced in the implant's conductive structures and current paths. If the implant's temperature rises too high, damage to the surrounding tissue may result. The implant devices of the present invention are configured to reduce the amount of heat generated during the battery's charging time and to extend the battery's lifetime.

As has been indicated, a preferred application for the present invention is with an implanted cochlear stimulation device. Hence, in the descriptions that follow, reference is frequently made to a cochlear implant device. However, it is to be emphasized that the invention is not limited to a cochlear implant device. Rather, the invention may be used within any implantable device wherein there is a need or desire to reduce eddy currents at a time when the implantable device is exposed to alternating magnetic flux of a type that would otherwise introduce eddy currents.

Referring to FIG. 2A, one embodiment of the invention is a cochlear implant device 10 that includes, in addition to the case 12, battery 14 and circuit 16, an implant lead 18 that extends from the case. The case houses the internal battery 14 and the signal processing circuit 16 and is surrounded by a coil 22, shown in FIG. 2B. A large portion of the case's internal cavity is occupied by the battery 14. The case is preferably implanted under the skin behind a patient's ear with the implant lead spiraling into the patient's cochlea. The implant lead has electrodes 20 for stimulating nerves within the cochlea with electrical pulses generated by the electronic circuit in response to audio sound signals from a microphone or the like thus allowing simulated hearing perception. A typical implant lead has between eight and thirty-two electrode pairs. Each electrode is connected to the circuit by the separate conductor.

The battery 14 is recharged using rectified ac power (or dc power converted from ac power through other means, e.g., efficient ac-to-dc converter circuits, also known as "inverter" circuits) received by the coil 22 that surrounds the case 12. To recharge the battery, an outside unit 15 that generates ac magnetic fields is placed against the outside of the patient's skin over the implant device 10. The ac magnetic fields 17 from the outside unit induce ac currents in the coil of the implant device. The coil is connected through ceramic insulated feedthrough pins to the electronic circuit 16 within the case which rectifies the ac current to produce dc current which is used to charge the battery with the power received through the coil. The ac magnetic fields, however, also induce heat generating eddy currents in the metal case (if metal), the electronic circuit, and the battery's electrode plates. Accordingly, the battery's recharging rate is limited by the maximum permissible case temperature, i.e., the ability of living tissue surrounding the implant to tolerate elevated temperatures. During battery recharging, a case temperature rise of only a few degrees centigrade can be extremely dangerous and cause damage to the surrounding living tissue.

To reduce the heat generated by the induced eddy currents in a metal case, the case 12 is fabricated of a biologically inert metal having a relatively high resistivity. Because the heat generated by the eddy currents is related to $i^2R$, where i is the current and R is the resistance, increasing the resistance R of the metal case decreases the magnitude of the eddy currents and accordingly decreases the heat generated by the eddy currents. Also, the thickness of the case shell or wall is minimized as much as structurally possible to further increase the resistance in the case shell or wall. Preferably, the metal case has a wall thickness of between 0.002 and 0.004 inches and is fabricated of Titanium$_{64}$ (6% aluminum, 4% vanadium). Titanium$_{64}$ has a resistivity of 177 micro-ohms centimeter which is about 60 times the resistivity of copper.

Alternatively, the case 12 may be fabricated of another metal such as Titanium$_{811}$ or (8% Aluminum, 1% Vanadium, 1% Molybdenum) Haines$_{25}$, or of a ceramic such as aluminum oxide (AlO$_x$) or zirconium oxide (ZiO$_x$) with ceramic insulated feedthrough pins. A ceramic case, however, would require thicker walls resulting in a larger implant device. Further, the case may be fabricated of a water resistant plastic with an internal water getter to absorb any moisture that may slowly leak through the plastic case.

The battery 14 is preferably a rechargeable lithium ion battery, or a nickel metal hydride (NiMH) battery. In an improved cochlear implant device 10 exemplary of the present invention, the implant lead electrodes 20 consume about 1 milliwatt (mW) of battery power and the electronic signal processing circuit 16 consumes about 6 mW of battery power. At these levels of power consumption, a 300 mW-hr battery will last about 50 hours (or about 2 days). A typical rechargeable lithium ion battery has a lifetime of about 500 recharging cycles and, if recharged every two days, would thus last only about 3 years. As discussed below, more frequent battery recharging may increase the battery's lifetime.

The heat generated by eddy currents induced on the battery's electrode plates is reduced by using plates 24 having elongated slits 26 cut through a substantial portion of the plates, as shown in FIG. 3A. Each electrode plate generally has a thickness of about 0.001 inches, a width of about 1 inch, and a length of about 1 inch. The slits are typically cut using a saw blade having a thickness of about 0.001 inches. Thus, after sawing, a gap of about 0.001 inches remains between the plate material resulting in a comb pattern of conductive teeth 28. The teeth may be configured to extend in a single direction or in many different directions. The spacing between the slits determines the width of the conductive teeth. To support higher magnetic fields associated with faster recharging rates, the slits should be spaced closely together resulting in narrower teeth. However, while cutting more slits through the plate generally results in smaller induced eddy currents, each cut lowers the conductive capacity of the plate and increases the battery's manufacturing cost. An advantageous conductive tooth width is about 0.040 inches with a gap of about 0.002 inches. The slit length may be shortened near a wire attachment point of the electrodes for increased current capacity near the wire attachment point. Also, the slit's gaps may be filled in with an insulative material such as nylon or polypropylene or other suitable insulation material. Additionally, the electrode plates, although shown in FIG. 3 as having substantially square surface, may have a variety of surface shapes and slit configurations that are effective in reducing the eddy currents and filling the case's cavity.

Figure 3B:
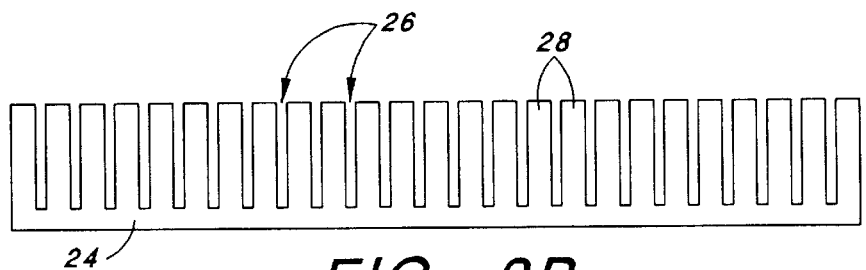
Figure 3C:
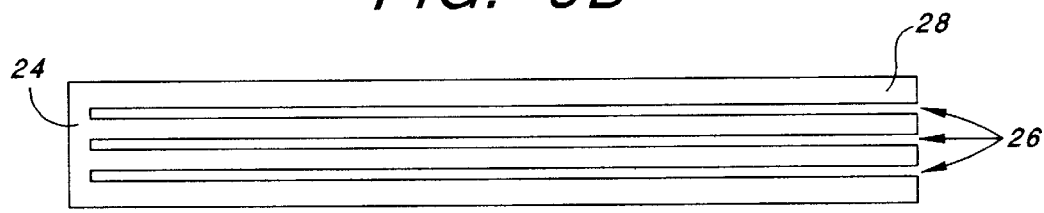

FIGS. 3B and 3C illustrate additional battery plates 24 that may be used with different shaped batteries. Each includes teeth 28 separated by slits 26 as described above.

Figure 3D:
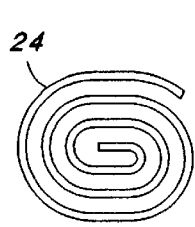
FIG. 3D illustrates one way in which the electrode plates shown in FIG. 3B and 3C may be rolled to form a small battery.

FIG. 3D shows the manner in which a small-sized battery may be formed by rolling the plates 24 of FIGS. 3B or 3C. Regardless of the shape or form factor of the battery, the goal of the invention remains the same: to use slits 26 in the plate 24 that prevent the formation of closed current loops, because it is the closed current loops that give rise to the undesired eddy currents.

As shown in FIG. 4, the battery 14 is built of cells consisting of alternating layers of first and second electrode plates, 30 and 32, respectively. A first separator 34 is formed of polypropylene and has tiny holes or pores that allows water and salts to pass through the separator, but that prevents larger molecules and metals from passing through it. Further, the first separator material may seal the electrode plates. A second separator 36 completely insulates each battery cell or layer from the adjacent cells above or below the layer. A relatively high-resistivity liquid paste is inserted between the electrodes and the separators. Because of the paste's relatively high resistivity, the amount of heat produced by eddy currents through the paste is very small.

The positive electrode is formed of aluminum and the negative electrode is formed of either silver or copper. Silver has slightly better conductivity (+5%) than copper, but is generally more expensive than copper. If an electrode uses an impregnated chemical compound matrix, the chemical compound matrix may be painted or coated onto the conductive teeth. Alternatively, the conductive teeth may be long thin wires that are cris-crossed with impregnated chemical strands.

As shown in FIG. 5, the entire metal case 12 is coated with a thin layer of Hysol epoxy 38 having a thickness of about 0.001 inches. The epoxy is a thermal insulator having a relatively low heat conductance in comparison with the heat conductance of the metal case. Thus, the epoxy layer allows the metal case to conduct heat from localized areas of relatively high temperature to cooler areas of the case before the heat can conduct through the epoxy layer preventing a substantial rise in the temperature of adjacent living tissue. Accordingly, the epoxy coating enables faster battery recharging rates because the ac induced heat generated at localized hot spots of the case is allowed to diffuse, resulting in surrounding living tissue adjacent the localized got spots being exposed to lower localized temperatures. Thus, an epoxy coated metal case will remain below the maximum permissible case temperature at higher charging rates.

Figures 6, 7:
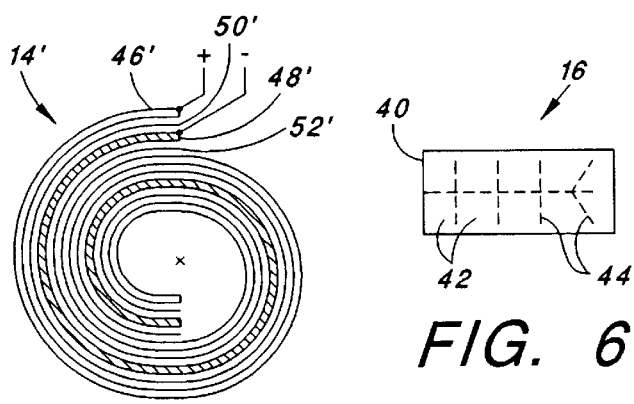
FIG. 6 is a plan view of a circuit board having predetermined circuit regions for reducing eddy currents in accordance with the present invention.
FIG. 7 is a plan view of a first embodiment of a spiral battery electrode configuration, in accordance with the present invention, for reducing induced eddy currents.

As seen in FIG. 6, the circuit 16 is laid out on a circuit board having circuit regions 42 and imaginary nonconductance lines or boundaries 44. The nonconductance lines prevent large circuit loops that may allow large eddy current loops to exist in the circuit. The circuit is laid out so that no components and conducting paths crossover the nonconductance lines, thereby precluding the formation of large eddy currents in the circuit. In a multilayer circuit board, the imaginary nonconductance line 44 should extend through all of the board's layers, or at least similar nonconductance boundaries or lines 44 should be imposed as a lay-out rules for each layer. Accordingly, the circuit layout is limited to the circuit regions, thus preventing large eddy currents in the circuit layout, and reducing the heat generated during battery charging to provide faster battery recharging times.

Figure 8:
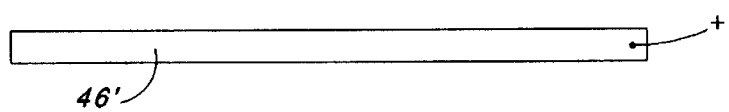
FIG. 8 is an elevation view of the battery electrode of FIG. 7, prior to rolling the electrode into the spiral configuration.

In an alternative embodiment of the invention, shown in FIGS. 7 and 8, the battery 14' is formed of a ribbon of long electrodes 46' and 48' and separators 50' and 52' wound [rolled] in a spiral configuration. In the plane of the spiral, the cross-sectional area of the thin electrodes is very small with no closed current loops along the length of either electrode, thus preventing large eddy currents from being induced in the electrodes during recharging through the coil 22.

Figure 9:
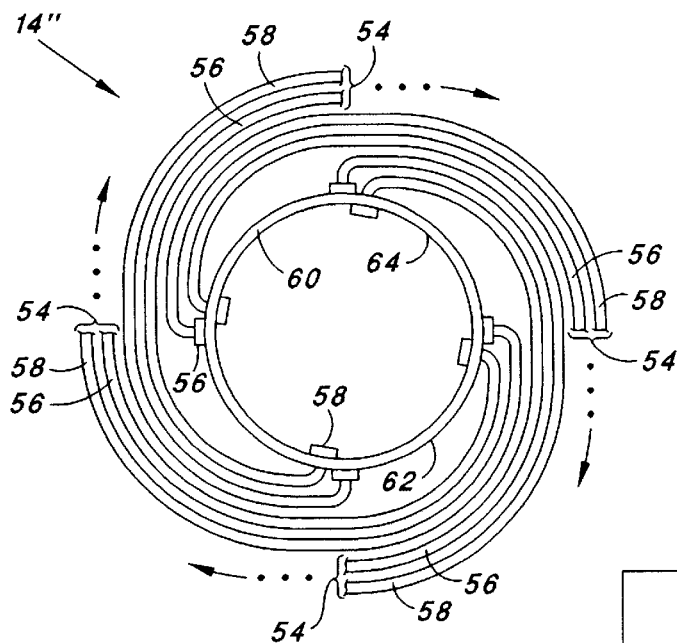
FIG. 9 is a plan view of a second embodiment of a spiral battery electrode configuration, in accordance with the present invention, for reducing induced eddy currents.
Figure 10:
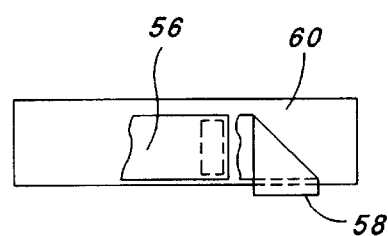
FIG. 10 is an elevation view of an electrode attachment ring for parallel electrode connection of the spiral battery of FIG. 9.

In a similar alternative embodiment of the invention, shown in FIGS. 9 and 10, the battery 14" is formed of four ribbon components 54 that are connected together in parallel and that are wound in a spiral configuration. Such configuration advantageously permits allows a much faster charging time that does, e.g., the configuration of FIG. 7. However, the cost of such faster charging time is a lower capacity, i.e., a lower battery current. The ribbon components of an actual battery are much longer than those shown in FIGS. 6 and 7. Also, for clarity, the necessary separators between the electrodes 56 and 58 are not shown. The resistance along a single ribbon may be significant at fast battery charging rates during which significant current flows through the ribbon and may result in chronic battery over charging of the ribbon near the battery's terminals or chronic undercharging of the ribbons at the open end. Dividing the ribbon into four shorter ribbons reduces any voltage differential along a single ribbon by a factor of four. Of course, more or fewer than four ribbons may be used in accordance with the present invention. The ribbons are connected in parallel through a center ring having an outer conductive surface 62 that is insulated from an inner conductive surface 64. The first or inner-most battery electrode 56 is connected to the outer conductive surface 62. The second or outer-most battery electrode 56 ends past the first electrode 58 extends past the first electrode and is folded at a right angle and wrapped under the center ring to contact only the inner conductive surface.

Figure 11:
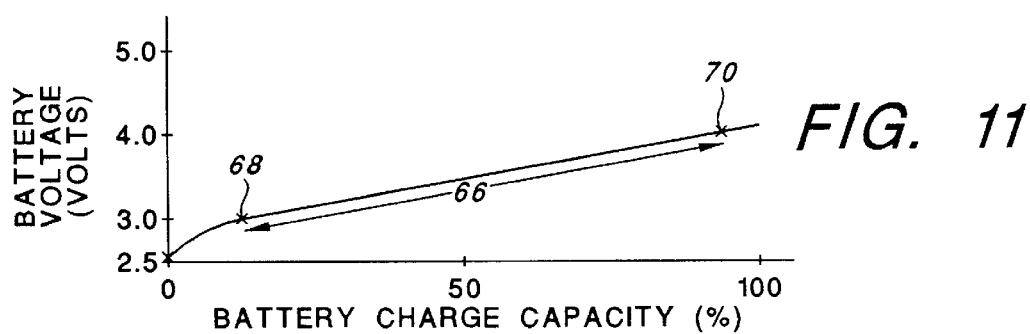
FIG. 11 is a graph of battery voltage verses battery charge capacity.

The rechargeable battery's lifetime may be improved by using it only in low stress regions 66 of its operational range, as shown in FIG. 11. More specifically, rechargeable battery cycle lifetime is based on the number of full discharges and charges or cycles that the battery 14 can perform while maintaining its power delivery specifications. For a lithium ion battery, a battery voltage of 2.55 volts indicates a fully discharged battery and a battery voltage of 4.1 volts indicates fully charged battery charge. However, fully discharging or fully charging the battery "stresses" the battery and limits its lifetime. Operating the battery within a relatively "low-stress" region 66 of the battery's operational range may significantly extend the battery's lifetime. For example, recharging the battery when its voltage drops to 3.0 volts (point 68 on the battery charging curve of FIG. 8.) and charging it to no more than 4.0 volts (point 70 on the battery charging curve) allows the battery to operate mainly within the low-stress regions of its operational range. Thus, even though the battery may have sufficient capacity to operate for two days between recharging, battery lifetime may be extended by daily or twice daily partial battery recharging.

Alternatively, a coulomb counter may be used instead of, or in addition to, a voltage level meter to monitor the battery's charge level. The coulomb counter may also indicate the battery's power efficiency.

Figure 12:
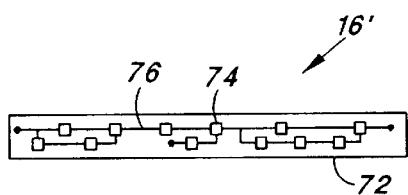
FIG. 12 is an elevation view of flexible circuit board prior to rolling it into a C-shaped or spiral configuration.
Figure 13:
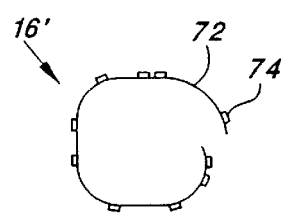
FIG. 13 is a plan view of the flexible circuit board of FIG. 12, rolled into a C-shaped or spiral configuration.

In accordance with the present invention, the circuit 16' may be laid out on a long narrow strip 72 of flexible material such as Kapton, as illustrated in FIG. 12. The circuit's components 74 and metalization traces 76 between the components are attached to the flexible strip. The flexible strip is then rolled into a C-shaped or spiral within the case 12, as shown in FIG. 13. As discussed above with respect to the spiral battery (FIG. 7), the C-shaped or spiral circuit 16' avoids large current loops that could result in large eddy current loops during battery charging.

Fully Implantable Systems

Fully implantable systems made in accordance with the present invention have been described previously in connection with FIGS. 1C, 1D and 1E.

FIG. 14A shows a plan view, and FIG. 14B a side view, of one type of partitioned fully implantable proximity system 160 (FIG. 1E). In the embodiment shown in FIGS. 14A and 14B, an ICS 112' is positioned proximate an implantable SP/PWR unit 162. The ICS 112' is housed within a ceramic case of the type described in U.S. Pat. No. 4,991,582, incorporated herein by reference. Ceramic, or an equivalent material, is preferably used for the case material to facilitate magnetic coupling through the case. A metal header 115 is hermetically sealed to one end of the ceramic case. Electrical feedthroughs positioned in the header 115 provide an hermetic electrical connection of the individual conductors of the cable 116 (which goes to the electrode array 114, not shown in FIGS. 14A or 14B) to the electrical circuitry housed within the ICS 112'.

The SP/PWR unit 162 is housed in a case which may be metallic, e.g., titanium, stainless steel, or similar material that is compatible with body tissues, as described above. Two electrical feedthroughs 176 pass through one side of the case and attach to a coil 172. The coil is aligned with and positioned over the coil that is included within the ICS 112'. The coil may be embedded within a suitable material, such as an encasing mold 174 made of silicone rubber or other suitable material, which mold is formed so as to adhere to the sides of the SP/PWR unit 162 and the ICS 112'. A complete-in-canal (CIC) microphone 134 is placed in the ear canal adjacent the implant location of the ICS 112' and SP/PWR unit 162. A telecoil link couples magnetic energy into the microphone which it uses as power to power its internal circuits. Sound (pressure waves) sensed by the microphone are converted to electrical signals which are transmitted via an RF transmitter or other suitable link the short distance to the SP/PWR unit 162. As needed, an external headpiece 136 (connected to an external programmer, not shown in FIG. 14B) may be positioned over the implant devices, on the outer side of the patient's skin 110, so as to override the internal speech processor, provide a charging or boosting current for the implant device, or to perform fitting and/or diagnostic functions.

An alternative embodiment of the fully implantable partitioned proximity system 160 (FIG. 1E) is illustrated in FIGS. 15A and 15B. FIG. 15A is a plan view of such embodiment, and FIG. 15B is a side or profile view. As seen in these figures, the ICS 112' and the SP/PWR unit 162 are placed side-by-side, proximate each other. Each unit has approximately the same thickness. Electrical feedthroughs 176' at one end of the SP/PWR unit 162 provide electrical connection for the coil 172'. Preferably, the coil 172' includes one or more turns of a suitable wire, e.g., a wire made from one of the noble metals, held together to form a cable or held within a suitable flexible conduit.

During the implant operation, the ICS 112' is implanted in conventional manner, and the SP/PWR unit is likewise implanted proximate thereto. The surgeon places the coil 172' so that it encircles the ICS 112', with the cable passing over the fantail portion the electrode array cable 116. The surgeon who performs the implant operation may suture the coil in place, as needed. A microphone 134, and an external headpiece 136 are used with the SP/PWR unit 162 and ICS 112' as described previously.

Figure 16:
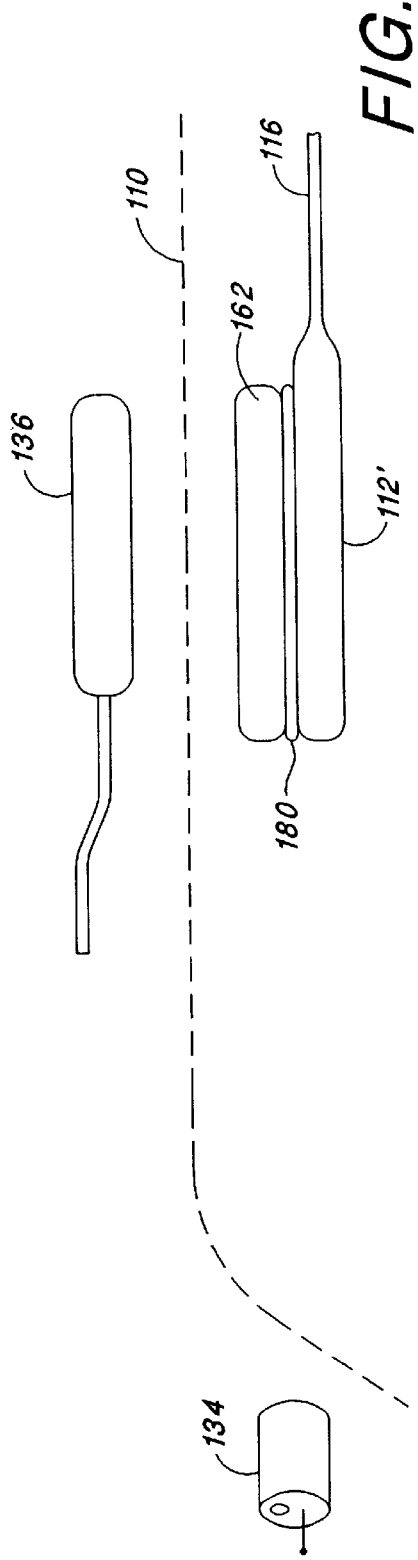
FIG. 16 is a profile view of yet another embodiment of a partitioned proximity system.

Yet a further embodiment of the fully implantable partitioned proximity system 160 (FIG. 1E) is illustrated in FIG. 16. As shown in FIG. 16, which shows a profile view of such embodiment, an ICS 112' and an SP/PWR unit 162 are stacked on top of each other. For the embodiment of FIG. 16, it is preferred that the SP/PWR unit 162 also have a ceramic case, like the ICS 112', or otherwise be designed, so that magnetic signals may pass therethrough without significant degradation. An advantage of the embodiment of FIG. 16 is that the SP/PWR unit 162 need not employ any hermetic feedthroughs. Rather, it may comprise a sealed hermetic unit having its coil inside of its case. A disadvantage of the embodiment of FIG. 16 is that the combined stack of the ICS 112' and the SP/PWR unit 162 are at least twice as thick as are the side-by-side embodiments, thereby requiring a deeper pocket to be formed in the patients tissue during implant, and perhaps resulting in a small bulge or bump on the patient's skin at the implant site.

During the implant operation for the embodiment of FIG. 16, the case of the SP/PWR unit 162 is simply placed over the ICS 112' so as to align its coil with the coil of the ICS 112'. If desired, a thin ferrite sheet 180, or a sheet made from other suitable low magnetic reluctance material, coated with a suitable protective, biocompatible material, may be inserted between the outer walls of the two units in order to help confine and focus the magnetic field associated with the inductive coupling to the desired area.

Figure 17:
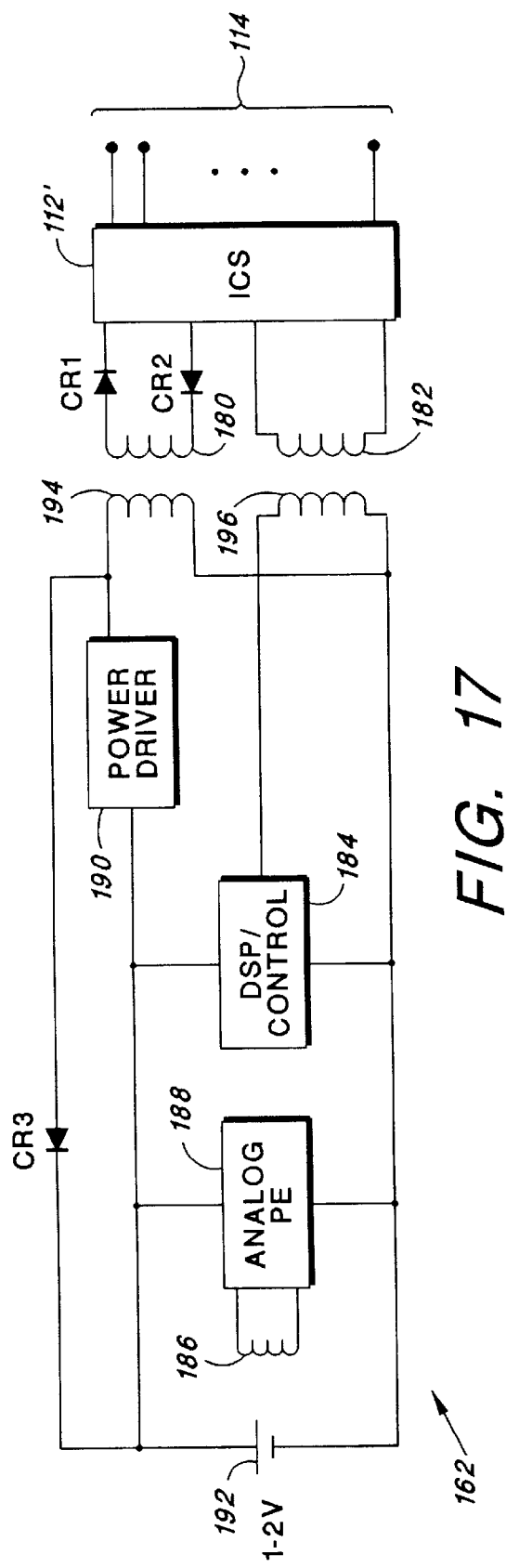
FIG. 17 illustrates a functional block diagram of the circuits used within a partitioned proximity system embodiment of the invention.

Turning next to FIG. 17, a simplified functional block diagram is illustrated of one embodiment of a proximity system 160 (FIG. 1E). It is to be emphasized that the configuration shown in FIG. 17 is functional, and is not intended to be limiting. It is submitted that those of skill in the art will readily be able to design circuitry that carries out the functions illustrated in FIG. 17 (as well as FIG. 18) given the teachings presented herein.

As seen in FIG. 17, the ICS 112' is attached to the electrode array 114, and also includes two coils 180 and 182. Coil 180 receives a carrier signal, rectifies it using diodes CR1 and CR2, and the rectified signal then provides operating power for the ICS. Coil 182 receives a modulated signal, which modulation contains the data that defines and controls the stimulation signals that are applied to individual electrodes of the electrode array.

The SP/PWR unit 162 includes a rechargeable battery 192, designed to operate at a nominal operating voltage of 1–2 volts. Such battery 192 provides operating power for the analog front end (FE) circuitry 188, digital signal processing (DSP) and control circuitry 184 and a Power Driver circuit 190. The power driver circuit 190 generates the carrier signal that is inductively or magnetically coupled into the ICS 112' via coils 194 and 180. The analog FE circuitry 188 receives signals from the microphone 134 via coil 186, amplifies and preliminarily processes such signals for presentation to the DSP/Control circuitry 184. The DSP/Control circuitry 184 applies a selected speech processing strategy to the sensed signals, generates the appropriate stimulation control signals for the ICS, and transfers such control signals to the ICS 112' through the magnetic link created by coils 196 and 182. Diode CR3 allows power received through coil 194 from an external headpiece 136 (e.g., during a recharging operation) that is in excess of the voltage of battery 192 to charge the battery 192.

When using a proximity system of the type shown in FIG. 17, the average battery life obtainable when such system is coupled to an ICS 112' of the type disclosed in the '726 patent, or equivalent system, assuming the indicated charge times per day, and the indicated battery type, is estimated to be as shown in Table 1.

TABLE 1

| | Estimated Battery Life | | | |
|---|---|---|---|---|
| | Average CIS | | Average SAS | |
| Implantable NiMH Battery Volume. | Battery Life | Charge Time/Day | Battery Life | Charge Time/Day |
| 12 × 25 × 6.7 mm | 6.3 years | 26 minutes | 4 years | 41 minutes |
| 17 × 36 × 6.1 mm | 8.1 years | 10 minutes | 5.2 years | 16 minutes |

The type of battery used in arriving at the data presented in Table 1 is an NiMH battery, or nickel metal hydride battery, a proven safe battery for implant purposes. In Table 1, it should be noted that "CIS" stands for "Continuous Interleaved Sampler" strategy, and is a particular type of speech processing strategy that stimulates only one electrode pair at any instant of time. "SAS", on the other hand, stands for a "Simultaneous Analog Stimulation" strategy, and is a type of speech processing strategy that may simultaneously stimulate many pairs of electrodes at the same time. Not surprisingly, and as shown in Table 1, an ICS operating in accordance with an SAS strategy consumes more power, and requires longer daily recharge times, than does an ICS operating in accordance with a CIS strategy.

Figures 18, 19:
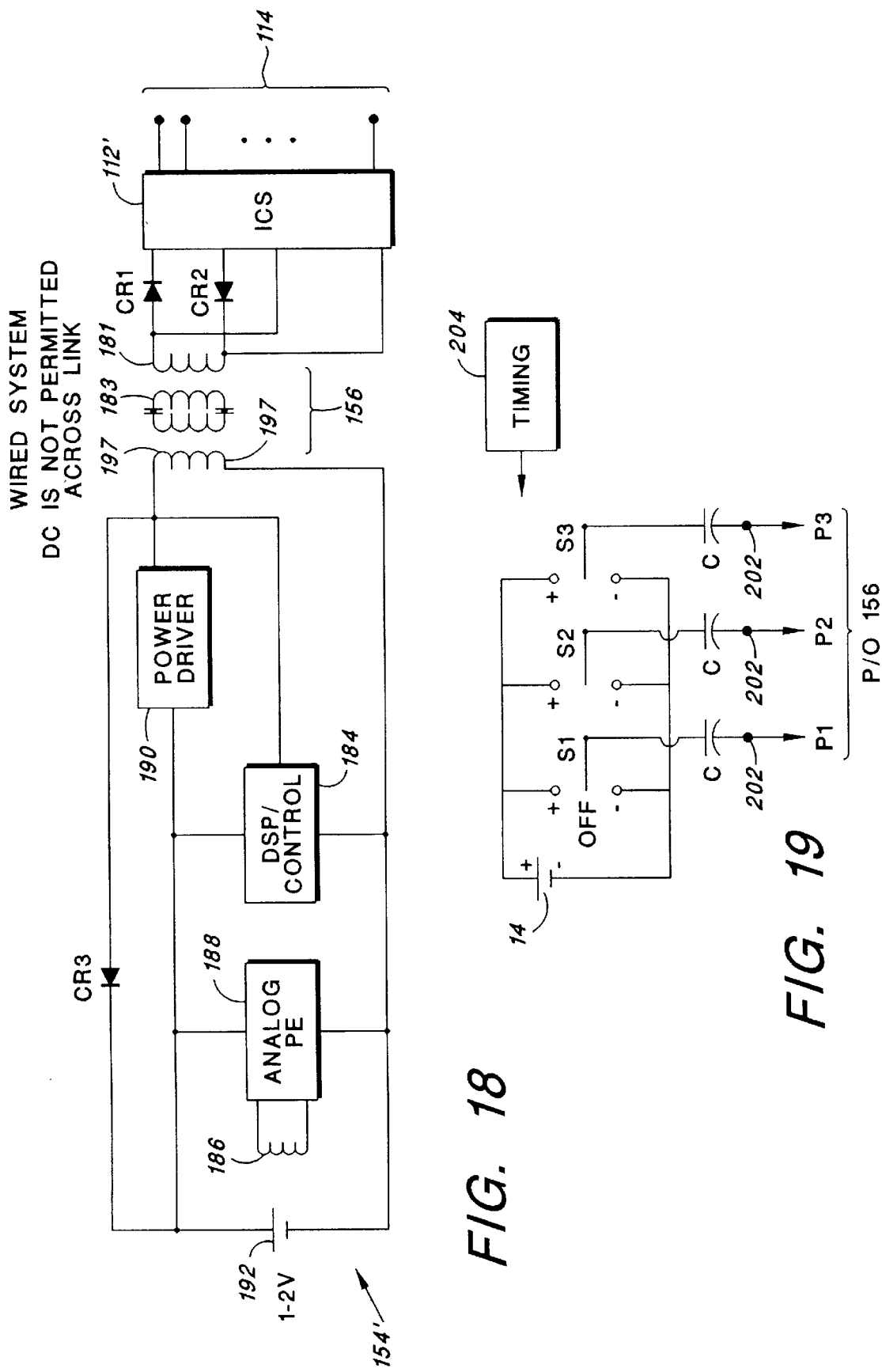
FIG. 18 similarly illustrates a functional block diagram of the circuits used within a partitioned wired system embodiment of the invention.
FIG. 19 shows a block diagram of a preferred 3-phase transmission system for transferring power between two implantable devices.

FIG. 18 illustrates a functional block diagram of the main circuits used within a wired system embodiment of the invention. For the most part, the block diagram of FIG. 18 includes circuits that perform the same functions as those described above in connection with FIG. 17. The main difference between the circuits of the wired system of FIG. 18 from the circuits of the proximity system of FIG. 17 is that the wired system utilizes a cable 156 to electrically connect the ICS 112' with a SP/PWR unit 154'. The cable shown in FIG. 18 includes only two conductors, and is transformer coupled on each end. That is, the coil 197, included within the hermetically sealed housing of the SP/PWR unit 154', is transformer coupled with a coil that is on the left end (as shown in FIG. 18) of the cable 156. Similarly, the coil 181, included within the hermetically sealed housing of the ICS 112', is transformer coupled with a winding that is on the right end of the cable 156. The conductors connected to the coils on the left and right ends of the cable 156 pass through suitable feedthrough connectors of their respective cases so that the cable itself is not hermetically sealed. At some point at the ends or along the length of the cable 156, a suitable connector is used that allows the cable to be detachably connected between the two implantable units. Such configuration thus prevents dc current from flowing across the link between the SP/PWR unit 154' and the ICS 112', which is desirable. Preferably, power is transferred through the cable 156 as an ac carrier signal, and data is transferred as modulation of the ac carrier signal.

It is noted that other variations of the connecting cable 156 may also be used, as explained previously. For example, the conductor may comprise a five or six conductor cable that allows data to be transferred between the two packages on two or three wires (conductors), while power is transferred on three wires (conductors) via a capacitor-coupled 3-phase square wave signal. In such instance, where capacitive-coupling is used at each end of the cable, transformer coupling is not required. Such capacitive-coupled cable does not allow dc current to flow outside of the hermetic seal of the packages, as desired. The 3-phase power signal, when received at the other package, is simply recombined to create a DC signal using synchronized switching without the need for filtering capacitors and with negligible ripple.

Figure 20:
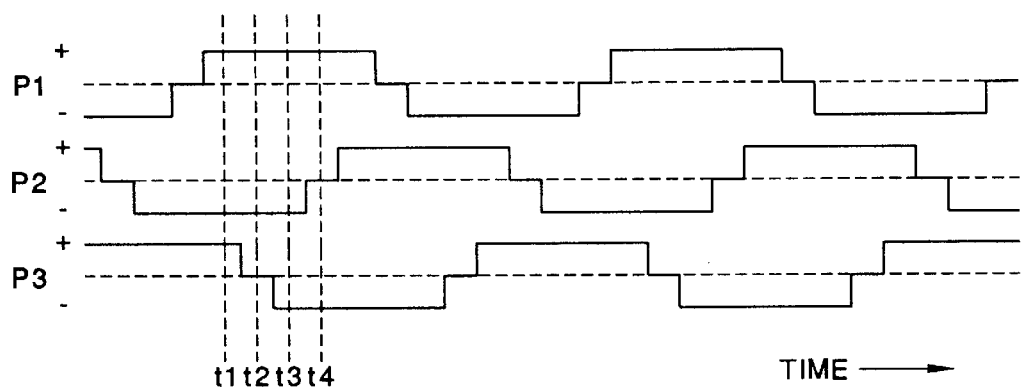
FIG. 20 is a waveform diagram illustrating the operation of the 3-phase transmission system of FIG. 19.

A preferred 3-phase transmission system for transferring power between two implant devices, such as the SP/PWR unit 154' and an ICS 112', is illustrated in FIGS. 19 and 20. FIG. 19 is a functional block diagram of such a 3-phase transmission system, and FIG. 20 is a waveform diagram that illustrates the operation of circuit of FIG. 19. As seen in FIG. 19, the battery 14 is connected to three switches S1, S2, and S3. (It is noted that while these switches are depicted as mechanical switches, including two terminals and an armature that is switched between the two terminals or to a floating position, in practice such switches are typically realized using solid state switching devices as is known in the art.) Each switch may assume a "+" position, a "0" (or OFF) position, and a "−" position. When in the "+" position, the armature of the switch is connected to the positive side of the battery 14. When in the "−" position, the armature of the switch is connected to the negative side of the battery 14. When in the "0" position, the switch is not connected to the battery 14 and is open. The armature of each switch is connected to a coupling capacitor C, and then to an electrical feedthrough pin or connector 202, which allows electrical connection to be made from a location inside of the hermetically-sealed case to the three conductors P1, P2 and P3 that form part of (p/o) the cable 156 outside of the hermetically sealed case and which interconnects the two implant devices of the wired system 150 (FIG. 1D).

In use, the switches are controlled using a conventional timing circuit (not shown) which connects one or two of the armatures to one side of the battery at the same time that the other armature is connected to the other side of the battery. During a phase transition, i.e., when one armature switches from one battery polarity to the other, the switch pauses in its "0" state to create a dead zone time when the armature is floating. This avoids introducing any switching transients on the armature lines, which in turn creates a clean dc voltage when the P1, P2 and P3 phases are recombined on the other end of the cable 156 in the other implant device. The advantage of using this approach is that the use of large filter capacitors, which would otherwise be needed in conventional rectifier circuit, can be avoided. Not having to use large filter capacitors is very desirable for a small volume implant device.

To illustrate the switching operation, reference is made to FIG. 20, which illustrates the voltage waveforms on the three phase conductors P1, P2 and P3. As seen in FIG. 20, at time t1, for example, P1 is connected to the "+" side of the battery, P2 is connected to the "−" side of the battery, and P3 is connected to the "+" side of the battery. At time t1, a timing circuit 204, which controls the operation of the three switches S1, S2 and S3, recognizes that switch S3 (connected to conductor P3) needs to begin its transition to the "−" side of the battery. Therefore, shortly after time t1, the switch S3 is changed to its "0" state, where it remains at time t2. This means the voltage on P3 decreases to zero and remains there until sometime after time t2, when switch S3 is switched to the "−" side of the battery. In the meantime, both P1 and P2 remain steadfastly connected to the "+" and "−" sides of the battery, respectively, providing a clean dc voltage signal on the other end of the cable through the P1 and P2 conductors. At time t3, switch S3 has completed its switching cycle, and is steadfastly connected to the "−" side of the battery 14, as is switch S2, meaning that at time t3 both P2 and P3 provide a "−" signal, while P1 provides a "+" signal. At time t3, however, the timing circuit 204 recognizes that switch S2 (connected to conductor P2) needs to begin its transition to the "−" side. Therefore, shortly after time t3, switch S2 is changed to its "0" state, where it remains at time t4. This means the voltage on P2 decreases to zero and remains there until sometime after time t4, when switch S2 is switched to the "+" side of the battery. This process or cycle continues as each of the three switches S1, S2 or S3, changes states between its "+" and "−" states by passing through its "0" state.

At the receiving end of the cable 156, within the other implant device, e.g., within the ICS 112', a similar switching circuit is used to recombine the signals to provide a desired dc voltage for powering the circuits found in the receiving implant device. In order to properly recombine the P1, P2, and P3 signals, appropriate synchronization is needed with the timing circuits within the first implant device (i.e., the timing circuits that were used to create the 3-phase signals found on the P1, P2 and P3 conductors). While such synchronization may be provided directly from the timing circuit 204 on a fourth conductor included within the cable 156, a preferred approach is to take the synchronization information from the P1, P2 or P3 signals themselves, thereby obviating the need for an extra conductor in the cable 156. That is, it is known at the receiving end of the cable 156 which conductor belongs to which phase, and the order or sequence of the switched phases. Thus, for example, by monitoring the P1 signal at the receiving end, it is possible to sense when the transition occurs between its "+" and "−" states. This transition, once detected, may then be used to trigger appropriate synchronization circuitry within the receiving implant device in order to faithfully reproduce the necessary timing signals for recombining the three phase signals P1, P2 and P3.

Although the present invention has been described in terms of a cochlear implant device, and while certain features of the invention are particularly suitable for use in a cochlear implant device, it is to be emphasized that the reduced eddy current features of the invention, as well as the fully implantable partitioned features of the invention (e.g., partitioning various functions into separate coupled implanted packages) may be applied to other implantable neural or muscular stimulation devices, or other implantable devices.

Thus, while the invention herein disclosed has been described by means of specific embodiments and applications thereof, numerous modifications and variations could be made thereto by those skilled in the art without departing from the scope of the invention set forth in the claims.

What is claimed is:

1. A rechargeable device for implantation within living tissue, comprising:

a case forming a substantially hermetic housing;

a coil that surrounds the case to enclose a relatively large area and that generates electrical power in the presence of externally induced ac magnetic fields passing through the coil's enclosed area;

a rechargeable battery, housed within the case, for storing electrical power from the coil and for providing electrical power for the device;

a circuit, housed within the case, that is laid out without forming relatively large current loops thus limiting heat generating eddy currents in the circuit resulting from the magnetic fields passing through the coil's enclosed area that also pass through the circuit.

2. A rechargeable battery that is subjected to externally induced ac magnetic fields, the battery comprising:

a substantially hermetic housing; and first and second electrodes, housed within the hermetic housing, for storing and providing electrical power, wherein each of the electrodes is configured to prevent forming relatively large current loops thus limiting heat generating eddy currents resulting from the ac magnetic fields passing through the battery, and wherein each electrode comprises a relatively flat conductive plate lying substantially in a plane; and wherein each electrode has slits in the flat plate to reduce the area of closed loops in the plane of the plate.

3. A rechargeable battery as defined in claim 2, further comprising a circuit board that is housed within the hermetic housing and that is laid out without forming relatively large current loops thus limiting heat generating eddy currents.

4. A cochlear implant device, comprising:

a relatively flat case;

an electronic circuit that is housed within the case and that generates electrical pulses for stimulating cochlear nerves within a patient's cochlea;

a coil that surrounds the case and lies substantially in a plane parallel with case's flat portion and that receives electrical power induced from external ac magnetic fields; and a battery that is housed within the case and that is coupled to the coil for battery recharging, the battery having first and second electrode plates, each electrode plate having a surface area that is relatively parallel to the plane of the flat case and that is configured to reduce the magnitude of eddy currents induced in the plate by the external ac magnetic fields during battery recharging.

5. A cochlear implant device as defined in claim 4, wherein the surface areas of the first and second electrode plates are relatively flat and have a length of about 1 inch and a width of about 1 inch.

6. A cochlear implant device as defined in claim 4, wherein the surface area of each electrode plate has a plurality of slits that extend across a substantial portion of the plate's surface area to produce regions of the surface area that each have a relatively long slender shape.

7. A cochlear implant device as defined in claim 6, wherein all of the slits are substantially parallel and form a comb of conductive teeth.

8. A cochlear implant device as defined in claim 7, wherein:

the conductive teeth have a width of about 0.040 inches; and the slits have a width of about 0.001 inches and a length of about 0.900 inches.

9. A cochlear implant device as defined in claim 8, wherein:

the slits form gaps between the conductive teeth, and the gaps are filled with an insulative material.

10. A cochlear implant device as defined in claim 9, wherein the insulative material is nylon.

11. A cochlear implant device as defined in claim 9, wherein the insulative material is polypropylene.

12. A cochlear implant device as defined in claim 4, wherein the case is formed of a metal material having a relatively high resistivity.

13. A cochlear implant device as defined in claim 4, wherein the case is formed of Titanium$_{64}$.

14. A cochlear implant device as defined in claim 13, wherein the case is coated with an epoxy material.

15. A cochlear implant device as defined in claim 14, further comprising a coil that encircles the case and that is embedded in the epoxy material, the coil for receiving externally induced ac power.

16. A cochlear implant device as defined in claim 15, wherein the battery is a lithium ion battery.

17. A cochlear implant device as defined in claim 16, further comprising a recharge control circuit that is connected between the coil and the battery for recharging the battery to about 4.0 volts using power received through the coil.

18. A cochlear implant device as defined in claim 15, further comprising a coulomb counter that measures the charge delivered to the battery during recharging and the charge delivered by the battery during discharge.

19. A cochlear implant device, comprising:

a case;

an implant lead that extends from the case and which is adapted to be inserted into a patient's cochlea, the lead having a plurality of electrodes for stimulating the patient's cochlear nerves; and a battery housed within the case, the battery having first and second electrode plates, each electrode plate having a surface area with a plurality of slits that extend across a substantial portion of the plate's surface area to produce areas having a relatively long slender shape thereby reducing, over a plate without slits of a similar surface area, the magnitude of eddy currents induced in the plate by external ac magnetic fields.

20. A cochlear implant device as defined in claim 19, wherein all of the slits are substantially parallel and form a comb of conductive teeth.

21. An implant device, comprising:

a relatively flat case;

electrical circuitry that provides a desired stimulating/sensing function;

recharging means for receiving electrical power induced from external ac magnetic fields; and a battery that is housed within the case and that is coupled to the recharging means and the electrical circuitry, the battery providing operating power to the electrical circuitry and having first and second electrode plates that are configured to reduce, in comparison with a battery formed of flat parallel electrode plates, the magnitude of eddy currents induced in the battery electrodes by external ac magnetic fields during battery recharging, wherein each battery electrode plate is relatively flat and has a plurality of slits that extend across a substantial portion of the electrode plate to produce regions of the electrode plate having a relatively long slender shape.

22. An implant device as defined in claim 21 wherein the recharging means includes a coil positioned inside of said case, and further including an external power source for coupling operating power to the coil to provide operating power to the electrical circuitry that supplements the operating power provided by the battery.

23. An implant device as defined in claim 21 wherein the recharging means includes a coil positioned inside of said case, and further including an external power source for coupling operating power to the coil to provide operating power to the electrical circuitry that replaces the operating power provided by the battery.

24. An implant system, comprising:

a first case;

electrical circuitry housed within the first case that provides a desired stimulating/sensing function;

a second case;

recharging circuitry that receives electrical power induced from external ac magnetic fields;

means for electrically coupling the first and second cases together; and a rechargeable power source housed within the second case that is coupled to the recharging means and the electrical circuitry, the power source providing operating power to the electrical circuitry.

25. The implant system of claim 24 wherein the rechargeable power source comprises a rechargeable battery.

26. The implant system of claim 25 wherein the rechargeable battery comprises a NiMH battery.

27. The implant system of claim 25 wherein the rechargeable battery has first and second electrode plates that are configured to reduce, in comparison with a battery formed of flat parallel electrode plates, the magnitude of eddy currents induced in the battery electrodes by external ac magnetic fields during battery recharging.

28. The implant system of claim 27 further including an external programming unit connected to the external headpiece for modulating the ac magnetic fields with control information.

29. The implant system of claim 24 wherein the coupling means comprises an inductive coupling scheme comprising a first coil associated with the first case and a second coil associated with the second case, the first and second coils being aligned with each other to allow ac signals to be coupled therebetween.

30. The implant system of claim 29 wherein the first coil resides inside the first case, and the second coil resides outside of the second case, but is electrically connected to circuitry within the second case.

31. The implant system of claim 30 wherein the second coil is embedded within a material that holds the coil against an outer surface of the first case.

32. The implant system of claim 30 wherein the second coil is looped around the first case.

33. The implant system of claim 30 wherein the first coil resides inside the first case, and the second coil resides inside the second case, and the first and second cases each comprise relatively flat cases that are stacked together.

34. The implant system of claim 24 wherein the coupling means comprises a detachable cable that electrically connects circuitry within the first case with electrical circuitry within the second case.

35. The implant system of claim 34 wherein the cable is transformer coupled at each end to the circuitry within the respective first and second cases.

36. The implant system of claim 34 wherein the cable is capacitively-coupled at each end to the circuitry within the respective first and second cases.

37. The implant system of claim 36 wherein the capacitively-coupled cable includes at least three conductors, and wherein 3-phase switching circuitry is used within the respective first and second cases to transfer power from the power source in the second case to the circuits within the first case.

38. The implant system of claim 24 further comprising an external headpiece coupled to an external power source for generating the ac magnetic fields for coupling into the recharging circuitry.

39. The implant system of claim 38 wherein the control information generated by the external programming unit overrides the stimulating/sensing function provided by the electrical circuitry housed within the first case, and provides a new stimulating/sensing function controlled by the external programming unit.

40. A rechargeable battery that is subjected to externally induced ac magnetic fields, the battery comprising:

a substantially hermetic housing; and first and second electrodes, housed within the hermetic housing, for storing and providing electrical power, wherein the first and second electrodes are each configured to prevent forming relatively large current loops, thus limiting heat generating eddy currents resulting from the ac magnetic fields passing through the battery, wherein the first and second electrodes comprise conductive ribbons that are coiled into a spiral without forming a closed loop along the spiral.

41. A rechargeable battery that is subjected to externally induced ac magnetic fields, the battery comprising:

a substantially hermetic housing; and first and second electrodes, housed within the hermetic housing, for storing and providing electrical power, wherein the first and second electrodes are each configured to prevent forming relatively large current loops, thus limiting heat generating eddy currents resulting from the ac magnetic fields passing through the battery, wherein the first electrode comprises four ribbons connected in parallel and the second electrode comprises four ribbons connected in parallel, wherein the four first electrode ribbons and the four second electrode ribbons are wrapped into a coiled spiral without forming a closed loop along the spiral.

42. A rechargeable battery that is subjected to externally induced ac magnetic fields, the battery comprising:

a substantially hermetic housing; and first and second electrodes, housed within the hermetic housing, for storing and providing electrical power, wherein the first and second electrodes are each configured to prevent forming relatively large current loops, thus limiting heat generating eddy currents resulting from the ac magnetic fields passing through the battery; and a circuit board housed within the hermetic housing that is laid out without forming relatively large current loops, thus limiting heat-generating eddy currents.

43. An implant device, comprising:

a relatively flat case;

electrical circuitry that provides a desired stimulating/sensing function;

recharging means for receiving electrical power induced from external ac magnetic fields; and a battery that is housed within the case and that is coupled to the recharging means and the electrical circuitry, the battery providing operating power to the electrical circuitry and having first and second electrode plates that are configured to reduce, in comparison with a battery formed of flat parallel electrode plates, the magnitude of eddy currents induced in the battery electrodes by external ac magnetic fields during battery recharging, wherein the first and second electrode plates comprise long thin electrodes that are coiled in a spiral.

44. An implant device as defined in claim 43, wherein the coiled first and second electrode plates are formed into a relatively flat pancake-like shape that occupies more than fifty percent of the case's interior volume.

45. An electrical stimulation/sensing system comprising:

electrical circuitry that provides a desired stimulating/sensing function for medical purposes;

a power source that provides operating power for the electrical circuitry;

two implantable cases, a first case and a second case;

the electrical circuitry that provides the desired stimulating/sensing function being housed in the first case;

the power source being housed within the second case; and means for electrically coupling the first and second cases together;

whereby the first case may be implanted in one location within body tissue, and the second case may be implanted in another location within body tissue, and power from the power source may be coupled into the electrical circuitry within the first case so that the electrical circuitry may carry out its intended stimulating/sensing function.

46. The fully implantable system of claim 45 wherein the power source comprises a rechargeable battery; and wherein the system further includes means for receiving primary power from an external source for recharging the rechargeable battery.

47. The fully implantable system of claim 46 wherein the rechargeable battery comprises a NiMH battery.

48. The fully implantable system of claim 45 wherein the electrical coupling means comprises an inductive coupling scheme comprising a first coil associated with the first case and a second coil associated with the second case, the first and second coils being aligned with each other to allow ac signals to be coupled therebetween.

49. The fully implantable system of claim 48 wherein the first coil resides inside the first case, and the second coil resides outside of the second case, but is electrically connected to circuitry within the second case.

50. The fully implantable system of claim 48 wherein the second coil is embedded within a material that holds the coil against an outer surface of the first case.

51. The fully implantable system of claim 48 wherein the second coil is looped around the first case.

52. The fully implantable system of claim 48 wherein the first coil resides inside the first case, and the second coil resides inside the second case, and the first and second cases each comprise relatively flat cases that are stacked together.

53. The fully implantable system of claim 45 wherein the coupling means comprises a detachable cable that electrically connects circuitry within the first case with electrical circuitry within the second case.

54. The fully implantable system of claim 53 wherein the detachable cable is transformer coupled at each end to the circuitry within the respective first and second cases.

55. An electrical stimulation/sensing system comprising:

electrical circuitry that provides a desired stimulating/sensing function for medical purposes;

a power source that provides operating power for the electrical circuitry;

two hermetically-sealed implantable cases, a first case and a second case;

the electrical circuitry that provides the desired stimulating/sensing function being housed in the first case;

the power source being housed within the second case; and a cable that electrically connects the electrical circuitry within the first case with the power source within the second case;

whereby the first case may be implanted in one location within body tissue, and the second case may be implanted in another location within body tissue, and power from the power source may be coupled into the electrical circuitry within the first case so that the electrical circuitry may carry out its intended stimulating/sensing function.

56. The system of claim 55 wherein the cable is detachable from at least one of the first or second cases.

57. The system of claim 56 wherein the power source comprises a rechargeable power source.

58. The system of claim 55 wherein the cable is capacitively-coupled at each end to circuitry within the respective first and second cases.

59. The system of claim 58 wherein the capacitively-coupled cable includes at least three conductors.

* * * * *